(12) United States Patent
Habuchi et al.

(10) Patent No.: US 11,639,896 B2
(45) Date of Patent: May 2, 2023

(54) SIZE CONTROLLABLE CONJUGATED POLYMER NANOPARTICLES WITH FLUORESCENCE IN THE SPECTRAL RANGE BETWEEN FAR-RED AND SHORT-WAVELENGTH INFRARED

(71) Applicant: King Abdullah University of Science and Technology, Thuwal (SA)

(72) Inventors: Satoshi Habuchi, Thuwal (SA); Hubert Marek Piwonski, Thuwal (SA); Tsuyoshi Michinobu, Tokyo (JP)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 574 days.

(21) Appl. No.: 16/631,010

(22) PCT Filed: Jul. 16, 2018

(86) PCT No.: PCT/IB2018/055260
§ 371 (c)(1),
(2) Date: Jan. 14, 2020

(87) PCT Pub. No.: WO2019/012514
PCT Pub. Date: Jan. 17, 2019

(65) Prior Publication Data
US 2020/0141868 A1  May 7, 2020

Related U.S. Application Data

(60) Provisional application No. 62/532,670, filed on Jul. 14, 2017.

(51) Int. Cl.
*G01N 21/64* (2006.01)
*C08G 61/12* (2006.01)
*C09K 11/06* (2006.01)

(52) U.S. Cl.
CPC ....... *G01N 21/6428* (2013.01); *C08G 61/126* (2013.01); *C09K 11/06* (2013.01);
(Continued)

(58) Field of Classification Search
CPC ....... G01N 21/6428; G01N 2021/6439; C08G 61/126; C08G 2261/18; C08G 2261/3223;
(Continued)

(56) References Cited

FOREIGN PATENT DOCUMENTS

| WO | 2016009231 | 1/2016 |
|---|---|---|
| WO | 2017042695 | 3/2017 |
| WO | 2017190345 | 11/2017 |

OTHER PUBLICATIONS

Michinobu et al. (Journal of Photopolymer Science and Technology vol. 30, No. 4 (2017) 495-499).*

(Continued)

*Primary Examiner* — Shane Fang
(74) *Attorney, Agent, or Firm* — Pabst Patent Group LLP

(57) ABSTRACT

Described are conjugated polymers and conjugated polymer nanoparticles formed therefrom. The conjugated polymers and conjugated polymer nanoparticles have a maximum emission of light that occurs within a tissue transparent window of the electromagnetic spectrum. These emission properties are particle-size independent. The sizes of the conjugated nanoparticles are controlled by altering the concentration of the conjugated polymer used to make conjugated polymer nanoparticles. Also described are methods of making conjugated polymer nanoparticles that have larger sizes than have been traditionally reported, involving a modified reprecipitation approach. The conjugated polymers and/or conjugated polymer nanoparticles can be used as fluorescent probes in biological imaging.

19 Claims, 8 Drawing Sheets

(52) U.S. Cl.
CPC . *C08G 2261/18* (2013.01); *C08G 2261/3223* (2013.01); *C08G 2261/3229* (2013.01); *C08G 2261/3241* (2013.01); *C08G 2261/3246* (2013.01); *C09K 2211/1458* (2013.01); *C09K 2211/1466* (2013.01); *C09K 2211/1483* (2013.01); *G01N 2021/6439* (2013.01)

(58) Field of Classification Search
CPC .... C08G 2261/3229; C08G 2261/3241; C08G 2261/3246; C09K 11/06; C09K 2211/1458; C09K 2211/1466; C09K 2211/1483
See application file for complete search history.

(56) References Cited

OTHER PUBLICATIONS

Wang et al., Macromolecules 2015, 48, 4012-4023.*
Leclerc et al. (Macro Lett. Apr. 21-24, 2015).*
Zou et al. (Macromolecules 2009, 42, 6361-6365).*
Path et al. (Macromol. Chem. Phys. 2010, 211, 1043-1053).*
Bruns, et al., "Next-generation in vivo Optical Imaging With Short-Wave Infrared Quantum Dots", Nat. Biomed. Eng., (2017).
Chen, et al., "Near-Infrared Fluorescent Semiconducting Polymer Dots with high Brightness and Pronounced Effect of Positioning Alkyl Chains on the Comonomers", ACS Applied Material & Interfaces, 6(23):21585-21595 (2014).
Feng, et al., "Conjugated polymer nanoparticles: preparation, properties, functionalization and biological applications", Chemical Society Reviews, 42(16):6620 (2013).
Geng, et al., "Biocompatible Conjugated Polymer Nanoparticles for Efficient Photothermal tumor Therapy", Small, 11(13):1603-1610 (2014).
Godin, et al., "Single-nanotube Tracking Reveals the Nanoscale Organization of the Extracellular Space in the Live Brain", Nat. Nanotechnol., 12:238-243 (2017).
Onk, "Synthesis of Benzotriazole Based Conjugated Polymers For Organic Light Emitting Diode and Organic Solar Cell", Thesis submitted to the Graduate School of Natural and Applied Sciences of Middle East Technical University, 82 pages (2016).
Qian, et al., "Design, synthesis, and properties of benzobisthiadiazole-based donor-[pi]-acceptor-[pi]-donor type of low-band-gap chromospheres and polymers", Canadian Journal of Chemistry, 88(3):192-201 (2010).
Qian, et al., "Near-Infrared chemiluminescence tunable from 900 nm to 1700 nm from narrow-bandgap compounds and polymers", Chemical Communications, 48(51 ):6426-6428 (2012).
Saager, et al., "Multilayer silicone phantoms for the evaluation of quantitative optical techniques in skin imaging", Proc. SPIE, 7567:756706 (2010).
Vasilis Ntziachristos, et al., "Going Deeper Than Microscopy: The Optical Imaging Frontier in Biology", Nature Methods, 7:603-614 (2010).
International Search Report for corresponding PCT application PCT/IB2018/055260 dated Nov. 9, 2018.

* cited by examiner

SIZE CONTROLLABLE CONJUGATED POLYMER NANOPARTICLES WITH FLUORESCENCE IN THE SPECTRAL RANGE BETWEEN FAR-RED AND SHORT-WAVELENGTH INFRARED

CROSS-REFERENCE TO RELATED APPLICATIONS

This application is a National Phase application under 35 U.S.C. § 371 of International Application No. PCT/IB2018/055260, filed on Jul. 16, 2018, which claims the benefit of and priority to U.S. Application 62/532,670 filed Jul. 14, 2017, the contents of which are incorporated by reference in their entirety.

FIELD OF THE INVENTION

Field of the Invention

The invention is generally in the field of imaging, particularly biological imaging using conjugated polymer nanoparticles as fluorescence probes, formed from conjugated polymers.

Background of the Invention

Imaging, in particular biological imaging, permits researchers to investigate physiological, metabolic, and/or pathological processes at the molecular or cellular levels. Fluorescence microscopy, involving fluorescence probes, is one of the most commonly used methods in biological imaging due to the high sensitivity with which fluorescence probes can be detected (Bruns, et al., Nat. Biomed. Eng., 2017; doi: 10.1038/s41551-017-0056). For instance, the distribution of a single molecule species can be determined, along with its amount and localization inside a cell using fluorescence microscopy.

However, technical limitations persist in fluorescence microscopy, especially in in vivo applications that involve imaging whole animals, deep tissue imaging, or both. These limitations include: autofluorescence of tissues or cells, which increases background signal, decreases image contrast, and therefore the sensitivity of fluorescence microscopy; and absorption and scattering of the excitation and emission light by blood and other tissues, which hinders signal detection and acquisition speeds (Bruns, et al., Nat. Biomed. Eng., 2017; doi: 10.1038/s41551-017-0056). In addition, mismatches in the refractive index, size, composition, and morphology of tissue components further contribute to light scattering that negatively impacts spatial resolution with increasing depth, giving rise to blurred images (Vasilis Ntziachristos, Nature Methods 2010, 7, 603-614; doi:10.1038/nmeth.1483). Another limitation of fluorescence microscopy resides in the types of fluorescent probe employed. As an example, quantum dots have been employed as fluorescent probes in tissue imaging, primarily due to their size-tunable fluorescent properties. However, one of the main drawbacks with quantum dots is that they contain metalloids or heavy metals such as cadmium, arsenic, zinc, and lead with their associated toxicities rendering quantum dots contraindicated for many biological applications. Accordingly, there remains a need to develop imaging tools, in particular biological imaging tools that can be used to efficiently investigate physiological, metabolic, and/or pathological processes.

Therefore, it is an object of the present invention to provide enhanced imaging tools.

It is another object of the present invention to provide probes with beneficial light absorption and/or emission properties.

It is a further object of the present invention to provide conjugated polymers and/or conjugated polymer nanoparticles with beneficial light absorption and/or emission properties, in particular conjugated polymers and/or conjugated polymer nanoparticles having a maximum emission of light within the far red and short-wavelength infrared region of the electromagnetic spectrum.

It is also an object of the present invention to provide methods of making conjugated polymers and/or conjugated polymer nanoparticles with beneficial light absorption and/or emission properties.

SUMMARY OF THE INVENTION

Conjugated polymers and conjugated polymer nanoparticles formed therefrom are disclosed. The conjugated polymers and conjugated polymer nanoparticles have a maximum emission of light occurring within the far-red (FR)/near infrared (NIR) spectral window (between 650 nm and 950 nm) spectral window, or short-wavelength infrared (SWIR) spectral window (between 1,000 nm and 1,350 nm) of the electromagnetic spectrum. The conjugated polymer nanoparticles do not contain toxic heavy metals such as cadmium, mercury, lead, and zinc that are commonly found in quantum dots. Altering the concentration of the conjugated polymer used to make conjugated polymer nanoparticles gives rise to size-controllable nanospheres with specific diameters, ranging between 1.0 nm and 50 nm, whose emission properties are independent of particle diameter.

The conjugated polymers have the structure:

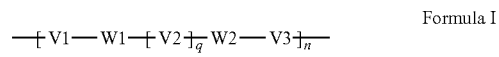

Formula I wherein:
n is an integer between 1 and 10,000; q is 1 or 2;
W1 is:

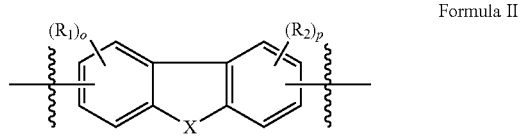

Formula II o and p are 1;
$R_1$ and $R_2$ are hydrogen, or $R_1$ and $R_2$ are tert-butyl;
X is $NR^3$ or $CR^4R^5$; $R_3$ is hexadecyl, $R_4$ and $R_5$ octyl;
W2 is

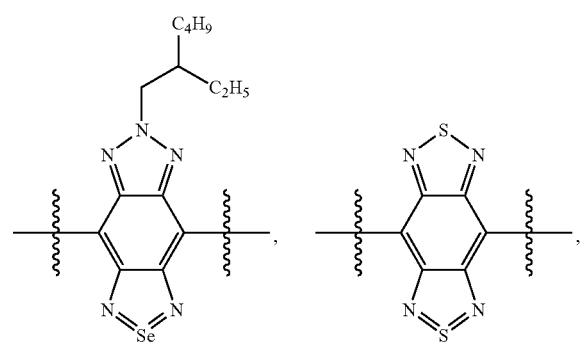

-continued

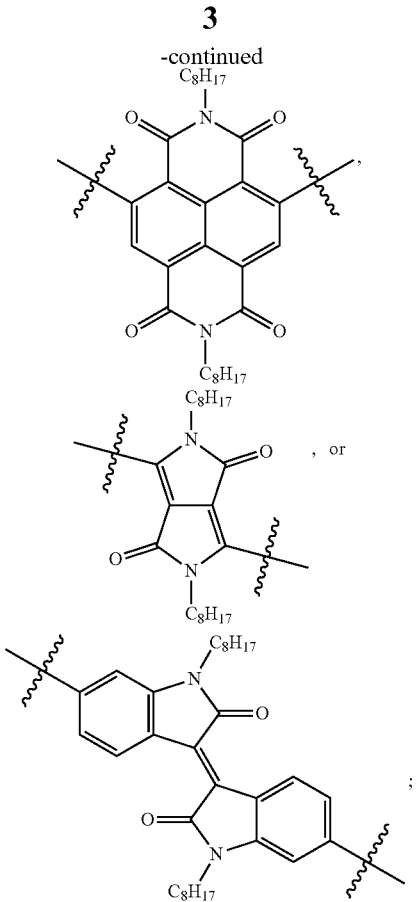

V1 is a carbon-carbon triple bond or thiazole; V2 is (i) a carbon-carbon triple bond, or a combination of (ii) thiazole and 3-octylthiophene, (iii) carbon-carbon triple bond and 3-(2-n-butyloctyl)thiophene, or (iv) carbon-carbon triple bond and thiophene; and V3 is absent, thiophene, or substituted heteroaryl (e.g. a five-membered ring substituted heteroaryl such as a 3-octylthiophene or 3-(2-n-butyloctyl) thiophene. Exemplary conjugated polymers are poly(dithiazolfluorene-alt-thiadiazolobenzotriazole) poly(dithiazolfluorene-alt-selenadiazolobenzotriazole), poly(carbozole-benzo[1,2-c;4,5-c']bis[1,2,5]thiadiazole) polymer, carbazole-diketopyrrolopyrrole polymer, carbazole-naphthalene diimide polymer, and carbazole-isoindigo polymer.

Also described are methods of making and using conjugated polymers and/or conjugated polymer nanoparticles that have larger sizes than have been traditionally reported, exhibiting far-red, near-infrared, and/or short-wavelength infrared emissions. The methods involve a modified reprecipitation approach. Nanoparticle size is controlled by altering the concentration of conjugated polymer solution used in the process. The conjugated polymers and/or conjugated polymer nanoparticles can be used as fluorescent probes in imaging applications, such as biological imaging.

BRIEF DESCRIPTION OF THE DRAWINGS

FIG. 1A, poly (dithiazolfluorene-alt-thiadiazolobenzotriazole) (PSN) (103A, 103B, 103C), and PSN Pdots (104A, 104B, 104C); FIG. 1B, poly(dithiazolfluorene-alt-selenadiazolobenzotriazole) (PSeN) Pdots dispersed in water; FIG. 1C, CBz-BBT polymer (107A, 107B), and CBz-BBT Pdots (108A, 108B); FIG. 1D, carbazole-diketopyrrolopyrrole (CBz-DPP) polymer (109A, 109B), and CBz-DPP Pdots (110A, 110B); FIG. 1E, carbazole-naphthalene diimide (CBz-NDI) polymer (111A, 111B), and CBz-NDI Pdots (112A, 112B); and FIG. 1F, carbazole-isoindigo (CBz-isoindigo) polymer (113A, 113B), and CBz-isoindigo Pdots (114A, 114B).

FIG. 2A shows a frequency histogram of the PSN Pdot size distribution from a 1:10 mixing ratio of THF containing PSN CP and water. FIG. 2B shows a frequency histogram of the PSN Pdot size distribution from the 1:1 mixing ratio of THF containing PSN CP and water. FIG. 2C shows a frequency histogram of the PSN Pdot size distribution from the 2:1 mixing ratio of THF containing PSN CP and water.

FIG. 4A shows the photoluminescence intensity time trajectories of a single PbS quantum dot (reference particles in the examples described below) deposited on a glass coverslip captured by both Si-based photodetector (visible wavelength region, top) and InGaAs-based photodetector (SWIR region, bottom). Top and bottom panels show large intensity fluctuations. FIG. 4B shows the photoluminescence intensity time trajectories of a single PSN Pdots deposited on a glass coverslip captured by both Si-based photodetector (visible wavelength region, top) and InGaAs-based photodetector (SWIR region, bottom). Top and bottom panels show nearly constant fluorescence intensity over time.

where S is fluorescence intensity at excitation power I, $S_\infty$ is maximum fluorescence intensity, and $I_s$ is the saturation excitation power at which fluorescence intensity is $S_\infty/2$.

Figure 5:
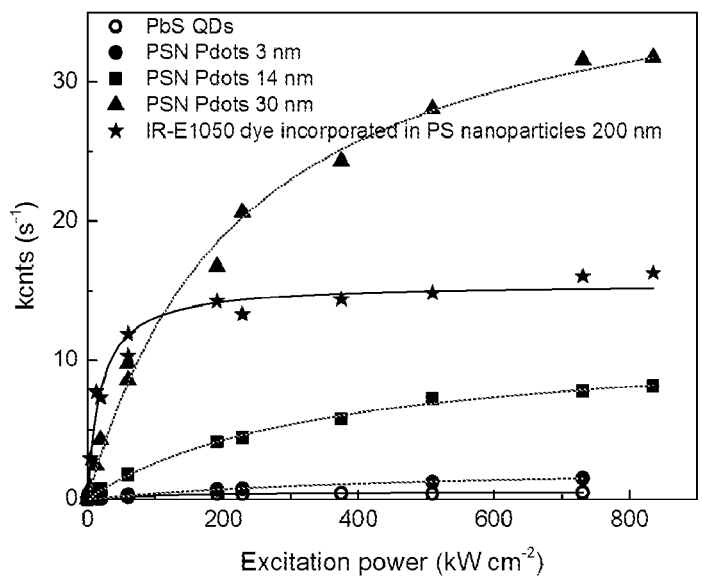
FIG. 5 is a line graph showing the excitation power-dependent fluorescence intensities of single SWIR-emitting nanoparticles deposited on a glass coverslip. Fluorescence signals from single nanoparticles excited at 785 nm were detected by a Si-based photodetector. Solid lines show fittings using the fluorescence saturation model $$S = S_\infty \frac{\left(\frac{I}{I_S}\right)}{\left(1 + \left(\frac{I}{I_S}\right)\right)}$$
Figure 6:
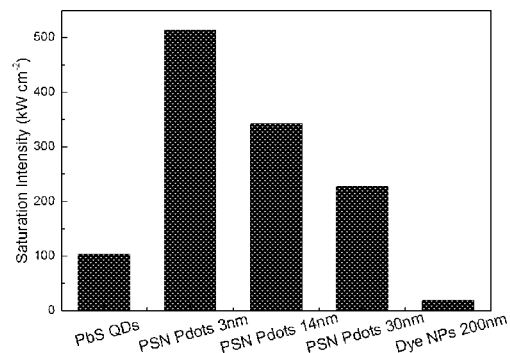

FIG. 6 is a column graph showing saturation intensities ($I_s$) determined by the fittings shown in FIG. 5.

Figure 7:
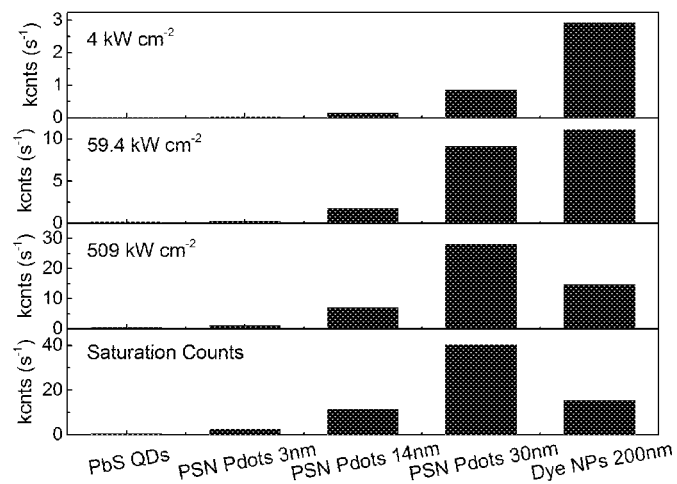

FIG. 7 is a column graph showing fluorescence count rates obtained from single fluorescent nanoparticles at 4 kWcm$^{-2}$, 59.4 kWcm$^{-2}$, and 509 kWcm$^{-2}$ excitation power. The bottom panel shows maximum fluorescence count rates expected for each nanoparticle.

Figure 8:
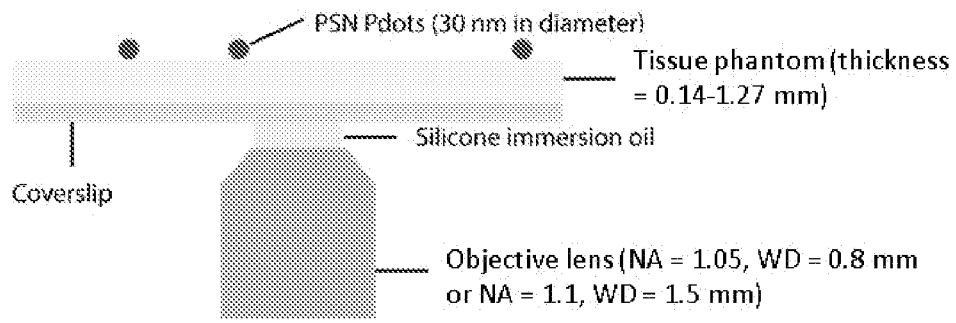

FIG. 8 is a schematic of the experimental setup used to detect fluorescence of PSN Pdots with increasing depth.

DETAILED DESCRIPTION OF THE INVENTION

I. Definitions

"Conjugated polymer" refers to an organic macromolecule containing a backbone chain of alternating covalent bonds selected from a single bond, a double bond, and a triple bond. An example can be alternating single- and double-bonds. Further, in some forms, the backbone chain containing alternating single- and double bonds, can also contain one or more triple bonds.

"Conjugated polymer nanoparticle" refers to a nanoparticle that contains a conjugated polymer. The conjugated polymer nanoparticles are also referred to as "Pdots."

"Hydrophilic" refers to the property of having affinity for water. For example, hydrophilic polymers (or hydrophilic polymer segments) are polymers (or polymer segments) that are primarily soluble in aqueous solutions and/or have a tendency to absorb water. In general, the more hydrophilic a polymer is, the more that polymer tends to dissolve in, mix with, or be wetted by water. Hydrophilicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in water than in the organic solvent, then the compound is considered hydrophilic. For example, if the organic solvent is octanol, then a negative log P value indicates that the compound is hydrophilic. "Hydrophilic" may also refer to a material that when applied to a surface, such as glass, forms a contact angle with water, which is less than the contact angle of water on a surface of glass without the material.

"Hydrophobic" refers to the property of lacking affinity for or repelling water. For example, the more hydrophobic a polymer (or polymer segment), the more that polymer (or polymer segment) tends to not dissolve in, not mix with, or not be wetted by water. Hydrophobicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in the organic solvent than in water, the compound is considered hydrophobic. For example, if the organic solvent is octanol, then a positive log P value indicates that the compound is hydrophobic. "Hydrophobic" may also refer to a material that when applied to a surface, such as glass, forms a contact angle with water, which is greater than the contact angle of water on a surface of glass without the material.

Hydrophilicity and hydrophobicity can also be quantitated in relative terms, such as, but not limited to, a spectrum of hydrophilicity/hydrophobicity within a group of polymers or polymer segments. In some forms wherein two or more polymers are being discussed, the term "hydrophobic polymer" can be defined based on the polymer's relative hydrophobicity when compared to another, more hydrophilic polymer.

A "macromolecule" can be a molecular structure containing one or more repeat units (monomers), connected by covalent bonds. The repeat units may all be identical, or in some cases, there may be more than one type of repeat unit present within the macromolecule.

"Particle" refers to an entity having a diameter of less than 10 μm. Particles include nanoparticles. "Nanoparticle" generally refers to a particle having a diameter, such as an average diameter, greater than or equal to 1 nm and less than 1 micron. The particles can have any shape. Nanoparticles having a spherical shape are generally referred to as "nanospheres."

"Polycyclic" refers to molecular structures containing ring systems having two or more cyclic rings in which two or more carbons are common to two adjoining rings (i.e., "fused rings").

"Small molecule" generally refers to an organic molecule that is less than about 2000 g/mol in molecular weight, less than about 1500 g/mol, less than about 1000 g/mol, less than about 800 g/mol, or less than about 500 g/mol. In some forms, small molecules are non-polymeric and/or non-oligomeric.

"Substantially background free imaging," as relates to fluorescence, describes a fluorescence intensity in which the ratio of signal to noise is greater than 90%. Useful examples of substantially background free imaging include fluorescence intensities in which the ratio of signal to noise is greater than 91%, 92%, 93%, 93%, 94%, 95%, 96%, 97%, 98%, or 99%. The fluorescence intensity can be measured using any means known in the art, such as with a fluorometer.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Alkyl," as used herein, refers to the radical of saturated aliphatic groups, including straight-chain alkyl groups, branched-chain alkyl, cycloalkyl (alicyclic), alkyl substituted cycloalkyl groups, and cycloalkyl substituted alkyl. In preferred forms, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Alkyl includes methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred forms, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; —NO$_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —CF$_3$, —CH$_2$—CF$_3$, —CCl$_3$); —CN; —NCOCOCH$_2$CH$_2$, —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls, —CN and the like. Cycloalkyls can be substituted in the same manner.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

The terms "alkoxyl" or "alkoxy," "aroxy" or "aryloxy," generally describe compounds represented by the formula —OR$^v$, wherein RV includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O— alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits. A "lower alkoxy" group is an alkoxy group containing from one to six carbon atoms.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkenyl" as used herein is a hydrocarbon group of from 2 to 24 carbon atoms and structural formula containing at least one carbon-carbon double bond. Asymmetric structures such as (AB)C=C(CD) are intended to include both the E and Z isomers. This may be presumed in structural formulae herein wherein an asymmetric alkene is present, or it may be explicitly indicated by the bond symbol C.

The term "alkynyl group" as used herein is a hydrocarbon group of 2 to 24 carbon atoms and a structural formula containing at least one carbon-carbon triple bond.

The term "aryl" as used herein is any $C_5$-$C_{26}$ carbon-based aromatic group, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, including, but not limited to, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, $-CH_2-CF_3$, $-CCl_3$), $-CN$, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, $-CH_2-CF_3$, $-CCl_3$), $-CN$, aryl, heteroaryl, and combinations thereof.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, $-CN$, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, $-CN$, aryl, heteroaryl, and combinations thereof.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aralkyl" as used herein is an aryl group having an alkyl, alkynyl, or alkenyl group as defined above attached to the aromatic group. An example of an aralkyl group is a benzyl group.

The term "hydroxyalkyl group" as used herein is an alkyl, alkenyl, alkynyl, aryl, aralkyl, cycloalkyl, halogenated alkyl, or heterocycloalkyl group described above that has at least one hydrogen atom substituted with a hydroxyl group.

The term "alkoxyalkyl group" is defined as an alkyl, alkenyl, alkynyl, aryl, aralkyl, cycloalkyl, halogenated alkyl, or heterocycloalkyl group described above that has at least one hydrogen atom substituted with an alkoxy group described above.

"Carbonyl," as used herein, is art-recognized and includes such moieties as can be represented by the general formula:

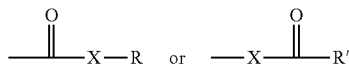

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R'', or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —(CH$_2$)$_m$—R''; R'' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, wherein one or more hydrogen atoms in R, R' or a group to which the moiety

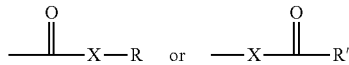

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "carboxyl" is as defined above for the formula

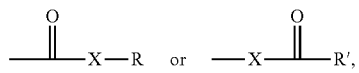

and is defined more specifically by the formula —R$^{iv}$COOH, wherein R$^{iv}$ is an alkyl, alkenyl, alkynyl, cycloalkyl, heterocyclyl, alkylaryl, arylalkyl, aryl, or heteroaryl. In preferred forms, a straight chain or branched chain alkyl, alkenyl, and alkynyl have 30 or fewer carbon atoms in its backbone (e.g., C1-C30 for straight chain alkyl, C3-C30 for branched chain alkyl, C2-C30 for straight chain alkenyl and alkynyl, C3-C30 for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, wherein one or more hydrogen atoms in R$^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenoxy" is art recognized, and refers to a compound of the formula —OR$^v$ wherein R$^v$ is (i.e., —O—C$_6$H$_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, wherein aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phenylthio" is art recognized, and refers to —S—C$_6$H$_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, wherein aryl and heteroaryl as defined herein.

The term "substituted arylthio" represents—S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The terms "amide" or "amido" are used interchangeably, refer to both "unsubstituted amido" and "substituted amido" and are represented by the general formula:

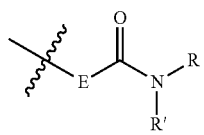

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide. In preferred forms, R and R' each independently represent a hydrogen atom, substituted or unsubstituted alkyl, a substituted or unsubstituted alkenyl, or —(CH$_2$)$_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

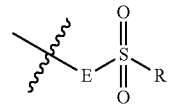

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —(CH$_2$)$_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of E and R can be substituted or unsubstituted amine, to form a "sulfonamide" or "sulfonamido" The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, wherein E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

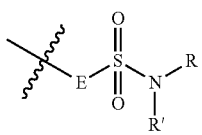

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred forms, only one of R and R' can be a carbonyl, e.g., R and R' together with the nitrogen do not form an imide.

The term "phosphonyl" is represented by the formula

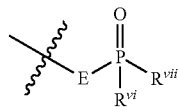

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R''', or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "phosphoryl" defines a phosphonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof. When two or more heteroaryls are involved, the chemical moiety can be referred to as a "polyheteroaryl."

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof. When two or more heteroaryls are involved, the chemical moiety can be referred to as a "substituted polyheteroaryl."

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The term "ether" as used herein is represented by the formula $AOA^1$, where A and $A^1$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "silyl group" as used herein is represented by the formula —SiRR'R", where R, R', and R" can be, independently, hydrogen, an alkyl, alkenyl, alkynyl, aryl, aralkyl, cycloalkyl, halogenated alkyl, alkoxy, or heterocycloalkyl group described above.

The terms "hydroxyl" and "hydroxy" are used interchangeably and are represented by —OH.

The terms "thiol" and "sulfhydryl" are used interchangeably and are represented by —SH.

The terms "cyano" and "nitrile" are used interchangeably to refer to —CN.

The term "isocyano" refers to —NCH.

The term "nitro" refers to —$NO_2$.

The term "phosphate" refers to —O—$PO_3$.

The term "azide" or "azido" are used interchangeably to refer to —$N_3$.

The disclosed compounds and substituent groups, can, independently, possess two or more of the groups listed above. For example, if the compound or substituent group is a straight chain alkyl group, one of the hydrogen atoms of the alkyl group can be substituted with a hydroxyl group, an alkoxy group, etc. Depending upon the groups that are selected, a first group can be incorporated within second group or, alternatively, the first group can be pendant (i.e., attached) to the second group. For example, with the phrase "an alkyl group comprising an ester group," the ester group can be incorporated within the backbone of the alkyl group. Alternatively, the ester can be attached to the backbone of the alkyl group. The nature of the group(s) that is (are) selected will determine if the first group is embedded or attached to the second group.

The compounds and substituents can be substituted with, independently, with the substituents described above in the definition of "Substituted."

II. Composition

Disclosed are conjugated polymers and nanoparticles (conjugated polymer nanoparticles) formed therefrom. Preferably, the CPs and conjugated polymer nanoparticles have a maximum emission of light occurring within the far-red (FR)/near infrared (NIR) spectral window (between 650 nm and 950 nm), or short-wavelength infrared (SWIR) spectral window (between 1,000 nm and 1,350 nm) of the electromagnetic spectrum. Emission in the FR/NIR and SWIR (i.e., between 600 nm and 1,350 nm, preferably between 650 nm and 1,350 nm) spectral range offers a tremendous opportunity for sensitive fluorescence imaging of thick tissue samples; whole body imaging, especially of small animals; and brain imaging. The present lack of biocompatible fluorescent probes is preventing the use of this highly sensitive spectral range for in vivo imaging applications. The Pdots described herein absorb and/or emit light in the FR/NIR/SWIR region.

These features of the Pdots can be advantageous in biological applications, such as in vivo imaging, where tissue samples can provide undesirable background signals. For instance, the first spectral window covers the tissue transparency window with wavelengths between 650 nm and 950 nm (FR/NIR), which is limited by the absorption of light by hemoglobin at short wavelengths and water at long wavelengths; the second spectral window which provides increased transparency for biological matter, encompasses wavelengths between 1,000 nm and 1,350 nm (SWIR). Detection of emitted photons in the FR/NIR/SWIR regions of the electromagnetic spectrum allows for reduced photon scattering and lower biological tissue absorption, and lower background signals due to autofluorescence, giving rise to substantially background free imaging of biological samples. Accordingly, Pdots can be used in deep tissue fluorescence imaging, such as single-particle deep tissue fluorescence imaging.

Preferably, the Pdots do not contain toxic components (e.g. toxic heavy metals such as cadmium, mercury, lead, and zinc) that are commonly found in quantum dots. The diameters of the Pdots can be controlled by altering the concentration of the conjugated polymer used to make the Pdots, varying the ratio of the volume of the conjugated polymer to water or aqueous solvent, or both. Generally, the Pdots have a diameter between 1.0 nm and 100 nm, inclusive. The Pdots can have any shape, but are preferably spherical.

The fluorescent properties of these first generation Pdots can be tuned based on the molecular design of the constituent conjugated polymers. Advantageously, the FR/NIR/SWIR fluorescence properties of the Pdots can be independent of particle-size, such that the emission properties of the Pdots are preferably not affected by the polydispersity (i.e., size distribution) of the Pdots. Therefore, in the production of the Pdots it is not required to include an experimental step to further isolate nanoparticles of a specific size so as to achieve a desired fluorescence property. This feature of the Pdots can distinguish them from quantum dots that show strong size-dependent fluorescence properties, and that constitute a majority of the previously reported photoluminescent nanoparticles that emit light in the SWIR region.

In some forms, the Pdots show higher saturation intensities compared to commercially available quantum dots (e.g. PbS quantum dots).

(1) Conjugated Polymers

The conjugated polymers have the structure:

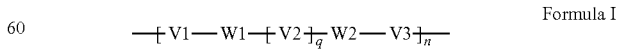

Formula I wherein:

n can be an integer between 1 and 10,000, inclusive, preferably between 5 and 10,000, inclusive;

q can be an integer between 1 and 5, inclusive, preferably 1 or 2;

W1 can be:

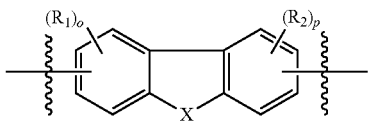

Formula II o and p can be independently integers between 1 and 3, inclusive, preferably 1;

$R_1$ and $R_2$ can be independently hydrogen, unsubstituted alkyl, substituted alkyl, unsubstituted aryl, substituted aryl, unsubstituted heteroaryl, substituted heteroaryl, hydroxyl, or halogen, preferably $R_1$ and $R_2$ are hydrogen, or $R_1$ and $R_2$ are substituted alkyl (e.g. $C_1$-$C_{10}$ substituted alkyl, such as tert-butyl);

X can be $NR_3$, $CR_4R_5$, O, or S, preferably X is $NR^3$ or $CR^4R^5$;

$R_3$, $R_4$, and $R_5$ can be independently hydrogen, unsubstituted alkyl, or substituted alkyl, preferably $R_3$ is unsubstituted alkyl (e.g. $C_1$-$C_{20}$ unsubstituted alkyl, such as hexadecyl), preferably $R_4$ and $R_5$ are unsubstituted alkyl (e.g. $C_1$-$C_{10}$ unsubstituted alkyl, such as octyl);

W2 can be one or more polycyclic ring systems, preferably having an unsubstituted heterocycle, substituted heterocycle, unsubstituted heteroaryl, or substituted heteroaryl, unsubstituted aryl, or substituted aryl;

optionally, the conjugated polymers can be as described above for Formula I with the exception that: (i) W2 is not unsubstituted carbazole, not substituted carbazole, not unsubstituted fluorene, or not substituted fluorene; (ii) W2 is not an unsubstituted carbazole, not substituted carbazole, not unsubstituted fluorene, or not substituted fluorene, when V1, V2, and V3 are all absent; (iii) W2 is not unsubstituted benzo[c][1,2,5]thiadiazole; (iv) W2 is not unsubstituted benzo[c][1,2,5]thiadiazole when W1 is an unsubstituted fluorene or substituted fluorene; or (v) when q is 1, V1 is absent, V2 and V3 are unsubstituted thiophene, and W2 is not unsubstituted benzo[c][1,2,5]thiadiazole;

V1, V2, and V3 can be independently absent, carbon-carbon double bond, carbon-carbon triple bond, unsubstituted heteroaryl, substituted heteroaryl, unsubstituted aryl, or substituted aryl, preferably, V1 is a carbon-carbon triple bond or unsubstituted heteroaryl (e.g. five-membered ring unsubstituted heteroaryl such as thiazole); preferably V2 is (i) a carbon-carbon triple bond, or a combination of (ii) unsubstituted heteroaryl (e.g. a five-membered ring unsubstituted heteroaryl such as a thiazole) and substituted heteroaryl (e.g. a five-membered ring substituted heteroaryl such as a 3-octylthiophene), (iii) carbon-carbon triple bond and substituted heteroaryl (e.g. a five-membered ring substituted heteroaryl such as a 3-(2-n-butyloctyl)thiophene, or (iv) carbon-carbon triple bond and unsubstituted heteroaryl (e.g. a five-membered ring unsubstituted heteroaryl such as thiophene); and preferably V3 is absent, an unsubstituted heteroaryl (e.g. a five-membered ring unsubstituted heteroaryl such as thiophene) or substituted heteroaryl (e.g. a five-membered ring substituted heteroaryl such as a 3-octylthiophene or 3-(2-n-butyloctyl)thiophene.

In some forms, the conjugated polymers having a structure of Formula I, as described above, can have an emission maximum of light in the far-red, near-infrared, or short-wavelength infrared region of the electromagnetic spectrum, or a combination thereof.

In some forms of the conjugated polymers having a structure of Formula I, as described above, X can be $CR^4R^5$ or $NR^3$, preferably $R_3$, $R_4$, and $R_5$ are independently unsubstituted alkyl or substituted alkyl, preferably $R_3$ is $C_1$-$C_{20}$ unsubstituted alkyl (such as hexadecyl); and preferably $R_4$ and $R_5$ are $C_1$-$C_{10}$ unsubstituted alkyl (such as octyl).

In some forms of the conjugated polymers having a structure of Formula I, as described above, W1 can be

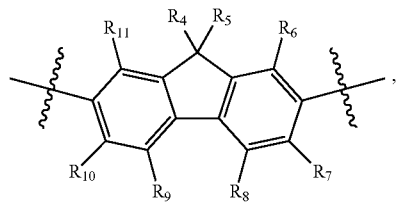

Formula III wherein $R_6$, $R_7$, $R_8$, $R_9$, $R_{10}$, and $R_{11}$ can be independently hydrogen, unsubstituted alkyl, substituted alkyl, unsubstituted aryl, substituted aryl, unsubstituted heteroaryl, substituted heteroaryl, hydroxyl, or halogen, preferably $R_6$, $R_7$, $R_8$, $R_9$, $R_{10}$, and $R_{11}$ are hydrogen.

In some forms of the conjugated polymers having a structure of Formula I, as described above, W1 can be

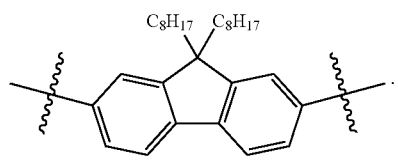

In some forms of the conjugated polymers having a structure of Formula I, as described above, W1 can be

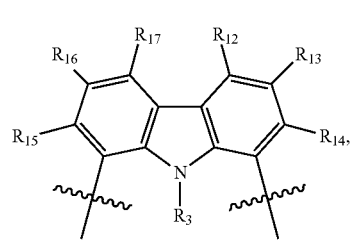

Formula IV wherein $R_{12}$, $R_{13}$, $R_{14}$, $R_{15}$, $R_{17}$, and $R_{17}$ are independently substituted alkyl, unsubstituted alkyl, hydrogen, unsubstituted aryl, substituted aryl, unsubstituted heteroaryl, substituted heteroaryl, hydroxyl, or halogen, preferably $R_{13}$ and $R_{16}$ are substituted alkyl, and $R_{12}$, $R_{14}$, $R_{15}$, and $R_{17}$ are hydrogen.

In some forms of the conjugated polymers having a structure of Formula I, as described above, W2 can be selected from

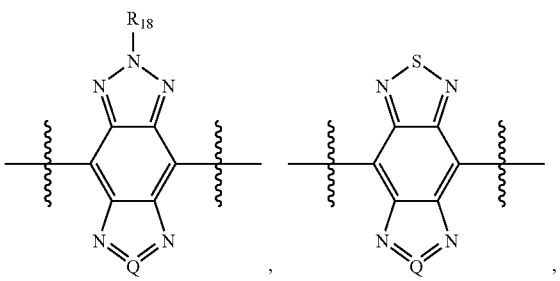

-continued

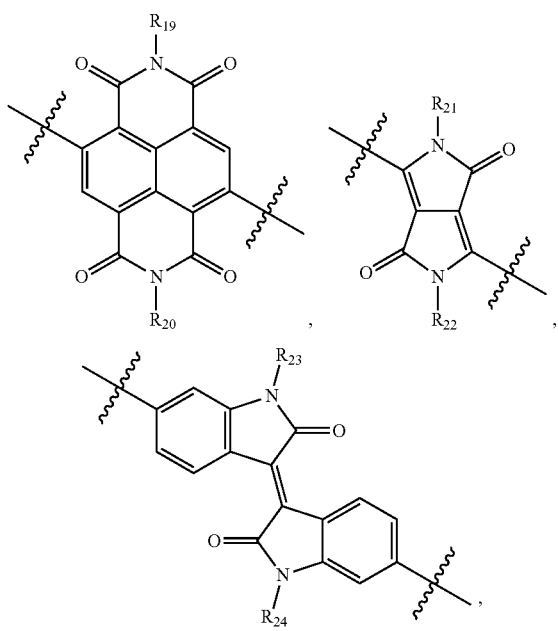

or a combination thereof, wherein Q can be sulfur or selenium; and $R_{18}$, $R_{19}$, $R_{20}$, $R_{21}$, $R_{22}$, $R_{23}$, and $R_{24}$ are independently unsubstituted alkyl, substituted alkyl, or hydrogen, preferably $R_{18}$ is substituted alkyl (e.g. $C_1$-$C_{10}$ substituted alkyl such as 2-ethylhexyl), preferably $R_{19}$, $R_{20}$, $R_{21}$, $R_{22}$, $R_{23}$, and $R_{24}$ are unsubstituted alkyl (e.g. $C_1$-$C_{10}$ unsubstituted alkyl such as octyl).

In some forms of the conjugated polymers having a structure of Formula I, as described above, W2 can be selected from

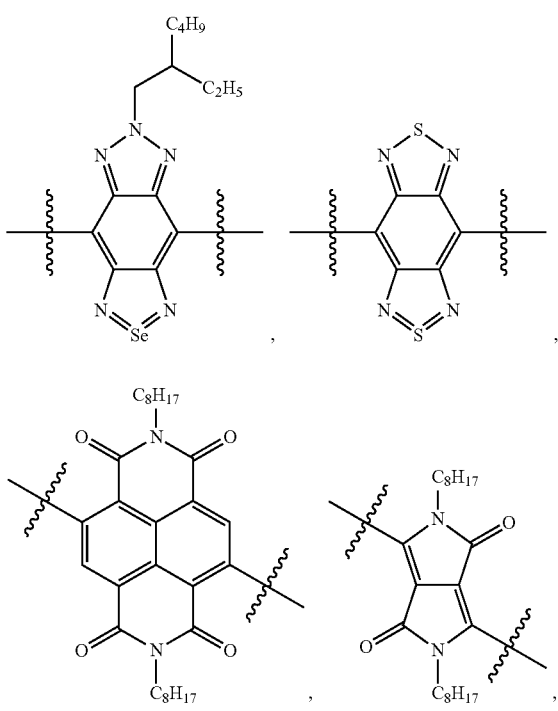

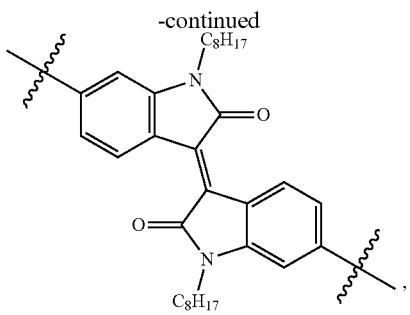

or a combination thereof.

In some forms of the conjugated polymers having a structure of Formula I, as described above, q can be 2.

In some forms of the conjugated polymers having a structure of Formula I, as described above, q can be 2, and V1, V2, V3 can be independently a carbon-carbon triple bond, unsubstituted heteroaryl, or substituted heteroaryl.

In some forms of the conjugated polymers having the structure of Formula I, as described above, q can be 2, V1 can be a carbon-carbon triple bond or unsubstituted heteroaryl (e.g. five-membered ring unsubstituted heteroaryl such as thiazole).

In some forms of the conjugated polymers having a structure of Formula I, as described above, q can be 2, V1 can be a carbon-carbon triple bond or unsubstituted heteroaryl (e.g. five-membered ring unsubstituted heteroaryl such as thiazole); and preferably V2 can be a combination of: (i) unsubstituted heteroaryl (e.g. a five-membered ring unsubstituted heteroaryl such as a thiazole) and substituted heteroaryl (e.g. a five-membered ring substituted heteroaryl such as a 3-octylthiophene); (ii) carbon-carbon triple bond and substituted heteroaryl (e.g. a five-membered ring substituted heteroaryl such as a 3-octylthiophene), or (iii) carbon-carbon triple bond and unsubstituted heteroaryl (e.g. a five-membered ring unsubstituted heteroaryl such as thiophene).

In some forms of the conjugated polymers having a structure of Formula I, as described above, q can be 2, V1 can be a carbon-carbon triple bond or unsubstituted heteroaryl (e.g. five-membered ring unsubstituted heteroaryl such as thiazole); preferably V2 can be a combination of: (i) unsubstituted heteroaryl (e.g. a five-membered ring unsubstituted heteroaryl such as a thiazole) and substituted heteroaryl (e.g. a five-membered ring substituted heteroaryl such as a 3-octylthiophene); (ii) carbon-carbon triple bond and substituted heteroaryl (e.g. a five-membered ring substituted heteroaryl such as a 3-octylthiophene), or (iii) carbon-carbon triple bond and unsubstituted heteroaryl (e.g. a five-membered ring unsubstituted heteroaryl such as thiophene); and preferably V3 can be an absent, unsubstituted heteroaryl (e.g. a five-membered ring unsubstituted heteroaryl such as thiophene) or substituted heteroaryl (e.g. a five-membered ring substituted heteroaryl such as a 3-octylthiophene or 3-(2-n-butyloctyl)thiophene.

In some forms of the conjugated polymers having a structure of Formula I, as described above, q can be 1.

In some forms of the conjugated polymers having a structure of Formula I, as described above, q can be 1, and V1 and V2 can be carbon-carbon triple bonds.

In some forms of the conjugated polymers having a structure of Formula I, as described above, q can be 1, V1 and V2 can be carbon-carbon triple bonds, and V3 can be absent.

In some forms, systematic control of fluorescence wavelength from FR to SWIR can be achieved by designing conjugated polymer molecules based on combinations of a carbazole (CBz) electron donor with a series of preferred polycyclic electron acceptor moieties. In some forms, the acceptor moieties are selected from benzo[1,2-c; 4,5-c']bis[1,2,5]thiadiazole, diketopyrrolopyrrole, naphthalene diimide, or a combination thereof. Exemplary combinations of a carbazole electron donor and polycyclic electron acceptors include: carbazole-benzo[1,2-c; 4,5-c']bis[1,2,5]thiadiazole (CBz-BBT), carbazole-diketopyrrolopyrrole (CBz-DPP), carbazole-naphthalene diimide (CBz-NDI), and carbazole-isoindigo (CBz-Isoindigo), also known as carbazole-(E)-1,1'-dioctyl-[3,3'-biindolinylidene]-2,2'-dione. To the best of our knowledge, systematic control of fluorescence wavelength in the NIR/SWIR has not been previously reported for CPs and/or Pdots. Therefore, in some forms of the conjugated polymers having a structure of Formula I, as described above, W1 is

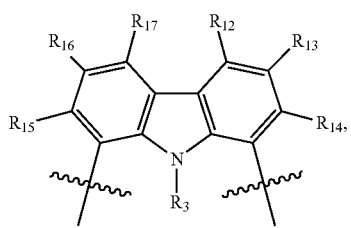

Formula IV wherein preferably $R_3$ can be unsubstituted alkyl (e.g. $C_1$-$C_{20}$ unsubstituted alkyl, such as hexadecyl);

preferably $R_{13}$ and $R_{16}$ can be substituted alkyl (e.g. $C_1$-$C_{10}$ substituted alkyl, such as tert-butyl), and $R_{12}$, $R_{14}$, $R_{15}$, and $R_{17}$ are hydrogen;

preferably, V1 can be a triple bond; preferably, at least one V2 can be a triple bond;

preferably W2 can be selected from

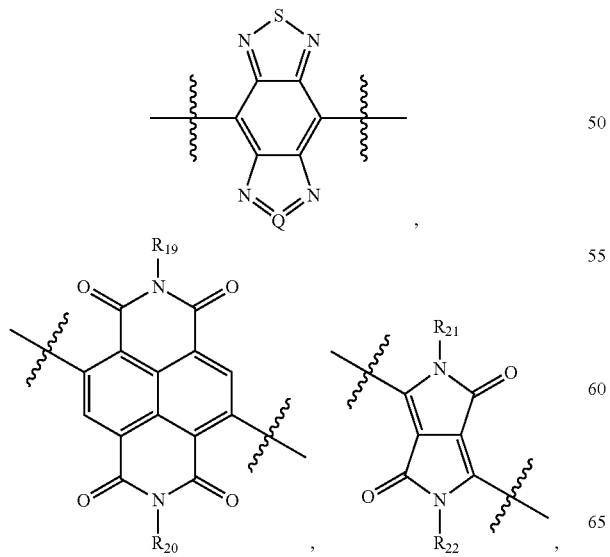

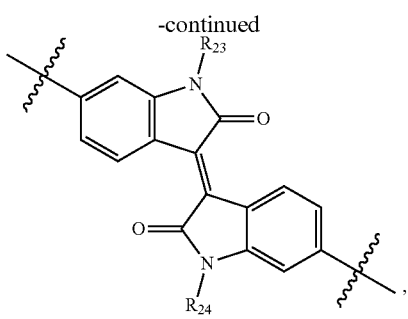

or a combination thereof,

Q can be sulfur or selenium; and $R_{19}$, $R_{20}$, $R_{21}$, $R_{22}$, $R_{23}$, and $R_{24}$ can be independently $C_1$-$C_{10}$ unsubstituted alkyl, such as octyl.

In some forms, the conjugated polymer can contain a structure selected from:

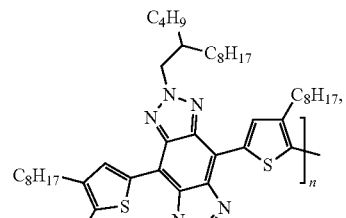

PSN

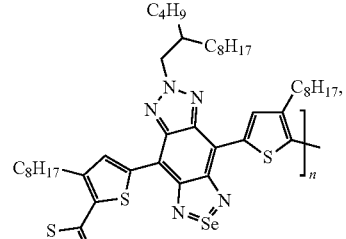

PSeN

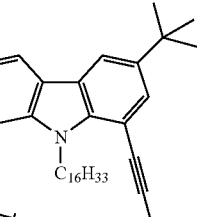

CBz-BBT

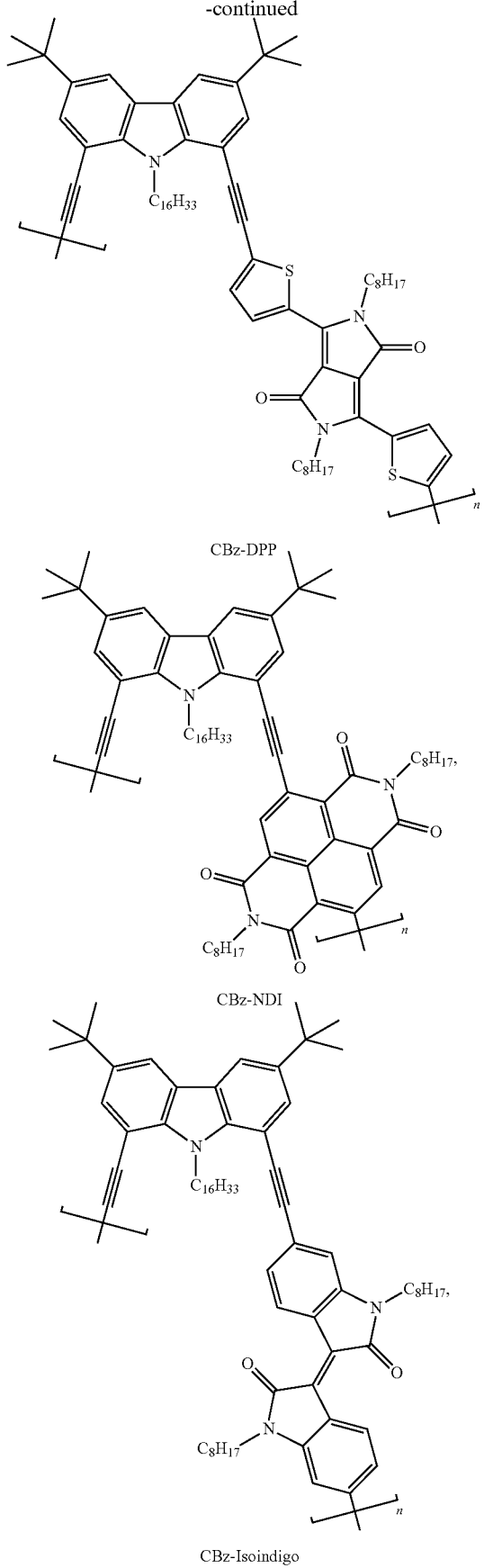

CBz-DPP

CBz-NDI

CBz-Isoindigo or a combination thereof, wherein n can be an integer between 1 and 10,000, inclusive, preferably between 5 and 10,000, inclusive.

Preferably the substituents of the substituted chemical groups of the conjugated polymers of Formula I, as described above, are selected from alkyl, alkenyl, alkynyl, aryl, heteroaryl, hydroxyl, halogen, alkoxy, aroxy, alkylthio, arylthio, cyano, isocyano, carbonyl, carboxyl, amino, amido, sulfonyl, sulfonic acid, phosphoryl, phosphonyl, polyaryl, unsubstituted $C_3$-$C_{20}$ cycloalkyl, and unsubstituted heterocyclyl.

(i) Properties

The conjugated polymers can have physical and/or optical properties that render the conjugated polymers useful in imaging applications, such as biological imaging. These properties include, but are not limited to molecular weight, hydrophobicity, and absorption and/or emission wavelengths. Preferably, the conjugated polymers are hydrophobic and/or include a polymer unit of Formula I, as described above.

(a) Molecular Weight

The number average molecular weight (Mn) of the conjugated polymers can be between 1 kDa and 50 kDa, inclusive, between 1 kDa and 40 kDa, inclusive, between 3 kDa and 35 kDa, inclusive. In some forms, the Mn is about 4.2 kDa, 4.6 kDa, 5.5 kDa, 12.6 kDa, 13 kDa, or 30 kDa. Mn can be measured using any means in the art, such as by gel permeation chromatography.

(b) Optical Properties

Preferably, the conjugated polymers absorb and emit light with a wavelength in the FR, NIR, and/or SWIR region of the electromagnetic spectrum, i.e., between 600 nm and 1,350 nm, inclusive, or between 650 nm and 1,350 nm, inclusive.

(2) Nanoparticles

Also described, are Pdots formed from the conjugated polymers of Formula I, described above. Exemplary conjugated polymers include: PSN and PSeN; as well as a newly synthetized series of CBz-based polymers, namely CBz-BBT, CBz-DPP, CBz-NDI, and CBz-isoindigo, described above. Further, the Pdots can be modified with other molecules to confer additional beneficial properties, such as in vivo circulatory half-life, tissue targeting, etc.

(a) Size

The sizes or diameters of the Pdots can be between 1.0 nm and 100 nm, inclusive, between 1.0 nm and 50 nm, inclusive, between 2.0 nm and 45 nm, inclusive, or between 3.5 nm and 31.9 nm, inclusive. In some forms, the diameters of the Pdots can be controlled by altering the concentration of the conjugated polymer in a solution used to make the Pdots by, for instance, varying the ratio of the volume of the conjugated polymer to water or aqueous solvent, or a combination thereof. As shown in the examples, the diameters of the Pdots with increasing conjugated polymer concentration used in fabricating the conjugated polymer nanoparticles.

(b) Optical Properties

In some forms, the Pdots emit light in the FR/NIR and SWIR region of the electromagnetic spectrum. Preferably, the emission maximum of light has a wavelength between 650 nm and 1,350 nm, inclusive, between 600 nm and 1,350 nm, inclusive, between 600 nm and 1,100 nm, inclusive, or between 650 nm and 1,100 nm, inclusive. Further, the region of the electromagnetic spectrum in which the emission maximum of light occurs can be independent of the size of the Pdot.

In some forms, the Pdots emit light in the FR/NIR and SWIR region of the electromagnetic spectrum and/or contain a CP selected from: PSN, PSeN, CBz-BBT polymer, CBz-DPP polymer, CBz-NDI polymer, CBz-isoindigo, or a combination thereof.

(c) Agents to Confer Additional Beneficial Properties

Preferably, the described conjugated polymers are hydrophobic. Optionally, the Pdots can include a molecule that confers a beneficial in vivo property to the Pdots, such as increased systemic circulation, or monitoring physiological processes. The molecule can be attached covalently or non-covalently to the conjugated polymer. In some forms, the molecule can be attached before or after formation of the Pdot.

In some forms, the molecule can be a hydrophilic molecule, such as a neutrally charged, hydrophilic molecule. Preferably, the neutrally charged, hydrophilic molecule increases the circulatory half-life (i.e., system circulation) of the Pdot. Neutrally charged, hydrophilic molecules include, but are not limited to poly(ethylene glycol), poly(vinyl alcohol), poly(hydroxyethyl acrylate), poly(hydroxyethyl methacrylate), and neutrally charged polysaccharides.

In some forms, the molecule can be one or more phospholipids. The phospholipids can partially or completely cover the surface of the Pdot.

(d) Targeting Agents

In some forms, the Pdots can include targeting moieties that selectively target the Pdots to a specific site, by specifically recognizing and binding to a target molecule specific for a cell type, a tissue type, an organ, or subcellular locale. Representative targeting moieties include, but are not limited to, antibodies and antigen binding fragments thereof, aptamers, peptides, and small molecules. The targeting moiety can be attached, covalently or non-covalently, to a conjugated polymer that forms the Pdot. Typically the targeting moiety is displayed on the surface of the Pdot. The targeting moieties should have an affinity for a cell-surface receptor or cell-surface antigen on the target cells. The targeting moieties may result in internalization of the Pdots within the target cell.

Preferably, the targeting moiety is associated with a disease or preferentially over-expressed in a diseased tissue or cell compared to a non-diseased tissue or cell. The target molecule can be a cell surface polypeptide, lipid, or glycolipid. In some forms, the target molecule can be a receptor that is selectively expressed on a specific cell surface, a tissue or an organ. Specific markers can be for specific types of cells including, but not limited to stem cells, skin cells, blood cells, immune cells, muscle cells, nerve cells, cancer cells, virally infected cells, and organ specific cells.

The agents to confer additional beneficial properties and targeting moieties can be used alone or in combination. For instance, the neutrally charged, hydrophilic polymer, phospholipid, and targeting moieties can be used alone or in any combination with each other, depending on the desired application.

Every CP or Pdot within the above definition is intended to be and should be considered to be specifically disclosed herein. Further, every subgroup that can be identified within the above definition is intended to be and should be considered to be specifically disclosed herein. As a result, it is specifically contemplated that any CP and/or Pdot or subgroup of CPs and/or Pdots can be either specifically included for or excluded from use or included in or excluded from a list of CPs and/or Pdots. For example, any one or more of the CPs and/or Pdots described herein, with a structure depicted herein, or referred to in the Tables or the Examples herein can be specifically included, excluded, or combined in any combination, in a set or subgroup of such CPs and/or Pdots. As an example, a CP and/or Pdot in which (i) W2 is unsubstituted carbazole, substituted carbazole, unsubstituted fluorene, or substituted fluorene; (ii) W2 is unsubstituted carbazole, substituted carbazole, unsubstituted fluorene, or substituted fluorene, and V1, V2, and V3 are absent; (iii) W2 is unsubstituted benzo[c][1,2,5]thiadiazole; (iv) W2 is benzo[c][1,2,5]thiadiazole when W1 is an unsubstituted fluorene or substituted fluorene; or (v) q is 1, V1 is absent, V2 and V3 are unsubstituted thiophene, and W2 is unsubstituted benzo[c][1,2,5]thiadiazole, can be specifically included or excluded, as a group or individually, from any CPs and/or Pdots per se (for example, a list or set of CPs and/or Pdots), compositions including the CPs and/or Pdots (including, for example, compositions for imaging), or any one or more of the disclosed methods, or combinations of these.

Preferably, the conjugated polymer nanoparticles have the sizes and/or optical properties discussed above. It should be noted that these optical properties are not dependent on the method of making the conjugated nanoparticles, but rather are heavily influenced by the constituent conjugate polymer.

III. Methods of Making (1) Conjugated Polymers

The conjugated polymers can be synthesized using methods such as palladium-catalyzed Stille polycondensation and palladium-catalyzed Sonogashira polycondensation. In a non-limiting example, PSN and PSeN were synthesized by palladium-catalyzed Stille polycondensation of (5,5'-(9,9-dioctyl-9H-fluorene-2,7-diyl)bis(thiazole-5,2-diyl))bis(tributylstannane) with 4,8-bis(5-bromo-4-octylthiophen-2-yl)-6-(2-ethylhexyl)[1,2,5]thiadiazole[3,4-f]benzotriazole and 4,8-bis(5-bromo-4-octylthiophen-2-yl)-6-(2-ethylhexyl)[1,2,5]selenadiazolo[3,4-f]benzotriazole, respectively. In another non-limiting example, CBz-BBT, CBz-DPP, CBz-NDI, and CBz-Isoindigo were synthesized by palladium-catalyzed Sonogashira polycondensation of 3,6-di-tert-butyl-1,8-diethynyl-9-hexadecyl-9H-carbazole and a dibromo-comonomer. Exemplary di-bromo-comonomers include: bis(2-bromo-3-(2-butyloctyl)thiophene)-substituted benzobisthiadiazole, to make CBz-BBT; 3,6-bis(5-bromothiophen-2-yl)-2,5-dioctyl-2,5-dihydropyrrolo[3,4-c]pyrrole-1,4-dione, to make CBz-DPP; 4,9-dibromo-2,7-dioctylbenzo[lmn][3,8]phenanthroline-1,3,6,8(2H,7H)-tetraone to make CBz-NDI; and (E)-6,6'-dibromo-1,1'-dioctyl-[3,3'-biindolinylidene]-2,2'-dione to make CBz-Isoindigo.

(2) Conjugated Polymer Nanoparticles

Also disclosed, are reliable and efficient methods of making Pdots from the conjugated polymers of Formula I (described above). Exemplary conjugated polymers of Formula I include PSN, PSeN, CBz-BBT, CBz-DPP, CBz-NDI and CBz-Isoindigo. The methods also afford the efficient control of the sizes of the Pdots.

The diameters of the Pdots can be altered by controlling the concentration of CPs in an organic solvent, varying the ratio of conjugated polymer solution to water or aqueous solution being mixed, or both. A preferred organic solvent is THF. A higher concentration of polymer in the organic solvent usually leads to larger particle size. In the case of FR/IR/SWIR emitting polymers, the larger size of the structural unit of the CPs used to obtain the low-band-gap (i.e., longer wavelength) emission leads to lower solubility of CPs in organic solvents. In particular, the major difficultly for fabricating NIR/SWIR emitting Pdots has been that the solubility of NIR/SWIR emitting CPs is generally quite low; therefore, NIR/SWIR emitting Pdots with sizes larger than 3.5 nm could not be obtained using the traditional approach. To the best of our knowledge, controlling the size of conjugated polymer nanoparticles that exhibit NIR/SWIR fluorescence has been met with difficulties.

A new approach was developed to fabricate NIR/SWIR emitting Pdots with larger sizes. The method involves a modified reprecipitation approach. By varying ratios of polymer in organic solvent and water during the reprecipitation process, variable sizes of generally spherical Pdots can be fabricated. Particle size is controlled by the concentration of conjugated polymer solution used in the process, with the particles increasing in size as the concentration of the conjugated polymer solution increases. Preferably, the conjugated polymer nanoparticles are bright, have a diameter between 1.0 nm and 100 nm, inclusive, display FR/NIR/SWIR fluorescence, or a combination thereof. Following the approach described herein, Pdots could be obtained having diameters of about 3.5 nm, 14.3 nm, and 31.9 nm.

The conjugated polymer nanoparticles can be made by dissolving a polymer in an organic solvent, preferably under sonication, and/or preferably at a low temperature, such as between 0° C. and 10° C., e.g. about 4° C. A preferred organic solvent can be tetrahydrofuran (THF). Sonication frequencies can be between 30 kHz and 45 kHz, inclusive, between 35 kHz and 40 kHz, inclusive, or any frequency there between, preferably about 37 kHz. Sonication can be maintained for a time frame between 30 minutes and 120 minutes, inclusive, between 45 minutes and 90 minutes, inclusive, or any time there between, preferably about 60 minutes. Preferably, the dissolved polymers forms a saturated solution of conjugated polymers in the organic solvent. In some forms, the saturated conjugated polymer solution can be filtered through a filter (e.g. a membrane filter such as a polycarbonate filter). In some forms, the filter has a pore size between 0.05 µm and 0.45 µm, inclusive, between 0.1 µm and 0.45 µm, preferably 0.1 µm. Preferably, filtering the saturated conjugated polymer solution is carried out using a 0.1-µm polycarbonate filter. The conjugated polymer solution can be mixed with water or aqueous solution, preferably under vigorous sonication and/or preferably at a temperature between 0° C. and 10° C., such as 4° C. to form conjugated polymer nanoparticles. Preferably, the water has been purified by filtration, ultrafiltration, distillation or deionization. Most preferably, the water is ultra-purified deionized water such as water treated by a Milli-Q water purification system (hereinafter Milli-Q water) or an equivalent ultra-purification system.

Varying ratios of the volume of conjugated polymer solution mixed with water maintained at a low temperature under vigorous sonication results in varied sizes of nanoparticles. Preferably, the dissolving step and/or the mixing step are performed at 4° C. Sonication in the dissolving step and the mixing step is preferably at a frequency between 30 kHz and 45 kHz. The size of the conjugated polymer nanoparticle can controlled by varying the ratio of conjugated polymer solution to water or aqueous solution mixed under sonication.

IV. Methods of Using

In some forms, the CPs having a structure of Formula I, as described above, and/or Pdots formed therefrom can be used as fluorescent probes in imaging applications, such as biological imaging. Exemplary biological imaging applications include: whole body imaging; single-particle (e.g. single-photon) deep tissue fluorescence imaging; metabolic imaging, generating blood flow maps, and diseased tissue imaging, e.g. tumors. Further, FR, NIR, and/or SWIR-emitting Pdots of variable sizes can be used for specific applications in tissue imaging or even for photoacoustic imaging.

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of disclosed forms. All parts or amounts, unless otherwise specified, are by weight.

EXAMPLES

Example 1: Preparation of Conjugated Polymers and Conjugated Polymer Nanoparticles Materials All chemicals were purchased from Tokyo Chemical Industry (TCI), Kanto, and Sigma-Aldrich and used as received.

Methods (a) Conjugated Polymers

A mixture of (5,5'-(9,9-dioctyl-9H-fluorene-2,7-diyl)bis(thiazole-5,2-diyl))bis(tributylstannane) (0.235 g, 0.07 mmol), 4,8-bis(5-bromo-4-octylthiophen-2-yl)-6-(2-ethylhexyl)[1,2,5]thiadiazolo[3,4-f]benzotriazole (0.173 g, 0.207 mmol), $Pd_2(dba)_3$ (0.015 g, 0.016 mmol), and $P(o-tolyl)_3$ (0.015 g, 0.048 mmol) in toluene (8 mL) was refluxed for 48 h under $N_2$. After cooling to room temperature, the reaction mixture was poured into methanol (200 mL). The precipitate was collected by filtration and purified with Soxhlet extraction using methanol, acetone, hexane, and chloroform. The chloroform soluble fraction was concentrated and precipitated into methanol, yielding PSN as a green solid (0.130 g, 51%). GPC (eluent: o-dichlorobenzene): $M_n$=30.0 kg mol$^{-1}$, $M_w/M_n$=2.38. $^1$H NMR (CDCl$_3$, 300 MHz): δ=8.72-8.10 (br, Th—H), 7.65-7.63 (br, Ar—H), 7.61-7.58 (br, Tz-H), 7.43-7.34 (br, Ar—H), 4.94-4.81 (br, N—CH$_2$), 2.98-2.95 (br, CH$_2$), 2.36-2.31 (br, CH), 2.10-2.08 (br, fluorene-CH$_2$), 1.85-1.80 (br, CH$_2$), 1.55-1.13 (br, CH$_2$), 0.91-0.81 (br, CH$_3$) ppm. IR (neat): ν=2956, 2924, 2852, 2363, 2341, 1558, 1541, 1521, 1507, 1466, 1435, 1397, 1319, 1260, 1189, 1089, 1018, 865, 792, 748, 727, 717, 670, 659, 612 cm$^{-1}$.

A mixture of (5,5'-(9,9-dioctyl-9H-fluorene-2,7-diyl)bis(thiazole-5,2-diyl))bis(tributylstannane) (0.148 g, 0.130 mmol), 4,8-bis(5-bromo-4-octylthiophen-2-yl)-6-(2-ethylhexyl)[1,2,5]selenadiazolo[3,4-f]benzotriazole (0.115 g, 0.130 mmol), $Pd_2(dba)_3$ (0.0010 g, 0.011 mmol), and $P(o-tolyl)_3$ (0.0010 g, 0.033 mmol) in toluene (6 mL) was refluxed for 48 h under $N_2$. After cooling down to room temperature, the reaction mixture was poured into methanol (200 mL). The precipitate was collected by filtration and purified with Soxhlet extraction using methanol, acetone, hexane, and chloroform. The chloroform soluble fraction was concentrated and reprecipitated into methanol, yielding PSeN as a dark brown solid (0.126 g, 76%). GPC (eluent: o-dichlorobenzene): $M_n$=12.6 kg mol$^{-1}$, $M_w/M_n$=2.21. $^1$H NMR (CDCl$_3$, 300 MHz): δ=8.71-8.10 (br, Th—H), 8.07-7.95 (br, Ar—H), 7.81-7.75 (br, Tz-H), 7.46-7.43 (br, Ar—H), 4.89-4.80 (br, N—CH$_2$), 2.90-2.73 (br, CH$_2$), 2.34-2.30 (br, CH), 2.13-2.10 (br, fluorene-CH$_2$), 1.78-1.70 (br, CH$_2$), 1.56-1.17 (br, CH$_2$), 0.92-0.80 (br, CH$_3$) ppm. IR (neat): vv=2954, 2921, 2852, 2364, 2342, 1558, 1541, 1507, 1456, 1436, 1397, 1378, 1312, 1261, 1186, 1103, 1018, 812, 756, 728, 718, 673, 651, 613 cm$^{-1}$.

A solution of 3,6-di-tert-butyl-1,8-diethynyl-9-hexadecyl-9H-carbazole (0.1134 g 0.2000 mmol) and bis(2-bromo-3-(2-butyloctyl)thiophene)-substituted benzobisthiadiazole (0.1706 g, 0.2000 mmol) in 3 mL toluene and 1 mL iPr$_2$NH was degassed with nitrogen for 15 min. PdCl$_2$(PPh$_3$)$_2$ (5.7 mg, 0.008 mmol) and CuI (1.5 mg, 0.008 mmol) were added. The reaction mixture was further degassed and then heated to 80° C. for 24 h. After cooling to room temperature, the mixture was poured into methanol. The precipitate was collected and washed with methanol and hexane. The precipitate was further subjected to Soxhlet washing with methanol to remove the low molecular fractions, yielding CBz-BBT (50%). GPC (eluent: THF): M$_n$=5.5 kg mol$^{-1}$, M$_w$/M$_n$=1.5. $^1$H NMR (300 MHz, CDCL$_3$): δ=8.12 (br, Ar—H), 7.72 (br, Ar—H), 5.49 (br, Ar—H), 2.92 (br, CH$_2$), 1.99 (br, CH), 1.74-0.78 (br, CH$_2$, CH$_3$) ppm. IR (neat): v=2956, 2924, 2854, 2361, 1450, 1427, 1259, 1186, 914, 869, 804, 741, 670 cm$^{-1}$.

A solution of 3,6-di-tert-butyl-1,8-diethynyl-9-hexadecyl-9H-carbazole (0.1134 g 0.2000 mmol) and 3,6-bis(5-bromothiophen-2-yl)-2,5-dioctyl-2,5-dihydropyrrolo[3,4-c]pyrrole-1,4-dione (0.1365 g, 0.2000 mmol) in 3 mL toluene and 1 mL iPr$_2$NH was degassed with nitrogen for 15 min. PdCl$_2$(PPh$_3$)$_2$ (5.7 mg, 0.008 mmol) and CuI (1.5 mg, 0.008 mmol) were added. The reaction mixture was further degassed and then heated to 80° C. for 24 h. After cooling to room temperature, the mixture was poured into methanol. The precipitate was collected and washed with methanol and hexane. The precipitate was further subjected to Soxhlet washing with methanol to remove the low molecular fractions, yielding CBz-DPP (78%). GPC (eluent: THF): M$_n$=4.2 kg mol$^{-1}$, M$_w$/M$_n$=1.9. $^1$H NMR (300 MHz, CDCL$_3$): δ=9.11 (br, Ar—H), 8.20 (br, Ar—H), 7.80 (br, Ar—H), 7.51 (br, Ar—H), 5.34 (br, Ar—H), 4.16 (br, CH$_2$), 1.97 (br, CH$_2$), 1.55 (br, CH$_2$), 1.35-1.16 (br, CH$_2$, CH$_3$), 0.91 (br, CH$_3$) ppm. IR (neat): v=2954, 2920, 2852, 2357, 2186, 1662, 1550, 1481, 1466, 1440, 1407, 1364, 1275, 1261, 1234, 1186, 1094, 1071, 1023, 913, 870, 814, 747, 667, 637 cm$^{-1}$.

A solution of 3,6-di-tert-butyl-1,8-diethynyl-9-hexadecyl-9H-carbazole (0.1134 g 0.2000 mmol) and 4,9-dibromo-2,7-dioctylbenzo[lmn][3,8]phenanthroline-1,3,6,8(2H,7H)-tetraone (0.1297 g, 0.2000 mmol) in 3 mL toluene and 1 mL iPr$_2$NH was degassed with nitrogen for 15 min. PdCl2(PPh$_3$)$_2$ (5.7 mg, 0.008 mmol) and CuI (1.5 mg, 0.008 mmol) were added. The reaction mixture was further degassed and then heated to 80° C. for 24 h. After cooling to room temperature, the mixture was poured into methanol. The precipitate was collected and washed with methanol and hexane. The precipitate was further subjected to Soxhlet washing with methanol to remove the low molecular fractions, yielding CBz-NDI (80%). GPC (eluent: THF): M$_n$=4.6 kg mol$^{-1}$, M$_w$/M$_n$=1.7. $^1$H NMR (300 MHz, CDCL$_3$): δ=8.95 (br, Ar—H), 8.22 (br, Ar—H), 8.06 (br, Ar—H), 4.24 (br, CH$_2$), 2.11 (br, CH$_2$), 2.07 (br, CH$_2$), 2.92-1.25 (br, CH$_2$), 1.16 (s, CH$_3$), 0.76 (s, CH$_3$) ppm. IR (neat): v=2954, 2918, 2851, 2366, 2328, 2173, 1703, 1664, 1562, 1483, 1443, 1396, 1363, 1313, 1224, 1181, 1103, 1026, 922, 875, 793, 722, 668, 636 cm$^{-1}$.

A solution of 3,6-di-tert-butyl-1,8-diethynyl-9-hexadecyl-9H-carbazole (0.1134 g 0.2000 mmol) and (E)-6,6'-dibromo-1,1'-dioctyl-[3,3'-biindolinylidene]-2,2'-dione (0.1289 g, 0.2000 mmol) in 3 mL toluene and 1 mL iPr$_2$NH was degassed with nitrogen for 15 min. PdCl$_2$(PPh$_3$)$_2$ (5.7 mg, 0.008 mmol) and CuI (1.5 mg, 0.008 mmol) were added. The reaction mixture was further degassed and then heated to 80° C. for 24 h. After cooling to room temperature, the mixture was poured into methanol. The precipitate was collected and washed with methanol and hexane. The precipitate was further subjected to Soxhlet washing with methanol to remove the low molecular fractions, yielding CBz-Isoindigo (75%). GPC (eluent: THF): M$_n$=5.5 kg mol$^{-1}$, M$_w$/M$_n$=1.6. $^1$H NMR (300 MHz, CDCL$_3$): δ=8.95 (br, Ar—H), 8.23 (br, Ar—H), 8.07 (br, Ar—H), 7.62 (br, Ar—H), 4.25 (br, CH$_2$), 4.00-1.10 (br, CH$_2$, CH$_3$), 0.76 (br, CH$_3$) ppm. IR (neat): v=3005, 2961, 2922, 2853, 2357, 2193, 1696, 1609, 1550, 1476, 1441, 1366, 1275, 1261, 1191, 1108, 1072, 1027, 913, 873, 849, 825, 668, 635 cm$^{-1}$.

(b) Conjugated Polymer Nanoparticles

Conjugated polymer nanoparticles of varied sizes were prepared according to the method described above. PSN conjugated polymers were dissolved in tetrahydrofuran (THF) organic solvent under continuous sonication maintained at a low temperature (4° C.) to produce a saturated PSN-THF solution, and the resulting saturated PSN-THF solution was filtered with a 0.1-μm polycarbonate filter. The saturated PSN-THF solution was mixed with Milli-Q water according to the ratios described for Preparations 1, 2, and 3, below. Mixing of the PSN-THF solution with the water was carried out at 4° C. under vigorous sonication and the resulting nanoparticle sizes were determined by transmission electron microscopy (TEM). Although Example 1 characterizes conjugated polymer nanoparticles containing PSN as the conjugated polymer, the size and distribution of conjugated polymer nanoparticles prepared with the other conjugated polymers described herein would show some minor variability from the PSN-conjugated polymer nanoparticles characterized here, but would be in the same general size range, Results FIGS. 1A-1F show the UV-VIS-FR/NIR/SWIR absorption and emission spectra of a series of FR/NIR and SWIR emitting CPs dissolved in THF and Pdots fabricated from those conjugated polymers that are dispersed in water with the intensity (101) plotted against wavelength (102) in nanometers. The emission spectra for the conjugated polymers in THF and the polymer nanoparticles range between 600 nm and 1,350 nm with emission peak maxima ranging between 660 nm and 1,040 nm. The conjugated polymers in THF and the polymer nanoparticles all had emission spectra in the FR/NIR/SWIR range within the tissue transparent spectral windows. Absorption peaks for the conjugated polymers in THF and the conjugated polymer nanoparticles range between 391 nm and 858 nm in the UV/VIS to NIR range.

Figure 1A:
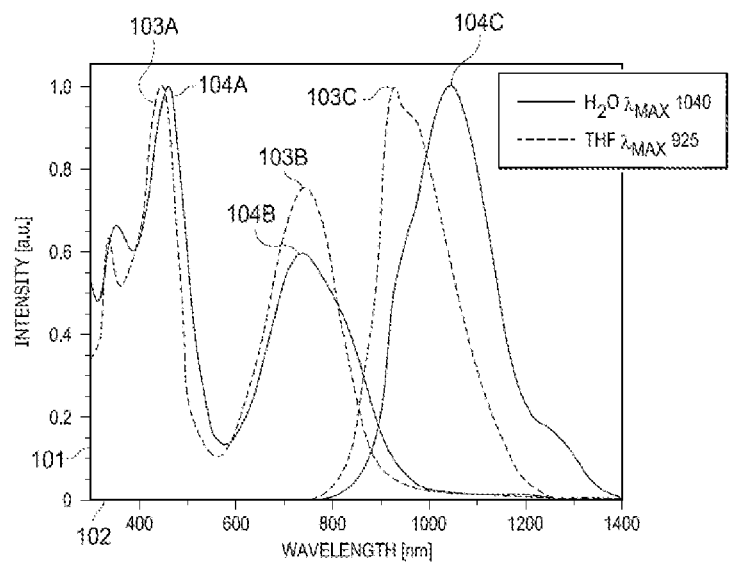
FIGS. 1A-1F are line graphs of the UV-VIS-FR/NIR/SWIR absorption and emission spectra of conjugated polymers (CPs) and/or conjugated polymer nanoparticles (Pdots). The CPs are dissolved in tetrahydrofuran (THF), while the Pdots are dispersed in water.

FIG. 1A shows that the absorption spectra of PSN has two major peaks with the first peaks located in visible (NIS) range with a maximum at 446 nm (103A) for PSN CP in THF and 460 nm (104A) for PSN Pdots in water. The second absorption peaks overlap with the first tissue transparent window with a maximum at 743 nm (103B) for PSN CP in THF and 735 nm (104B) for PSN Pdots in water.

The PSN emission spans the range between 830 nm and 1,300 nm with maxima of 925 nm (103C) for PSN CP in THF and 1,040 nm (104C) for PSN Pdots in water. The fluorescent properties of PSN Pdots fit in the second tissue transparent spectral window (between 1,000 nm and 1,350 nm), which allows for NIR/SWIR imaging with commercially available InGaAs-based photodetectors that have a sensitivity covering the typical range between 950 nm and 1,600 nm. Since the spectral detection sensitivity reaches up to 1,000 nm, PSN Pdots were also detected with Si-based photodetectors.

Figure 1B:
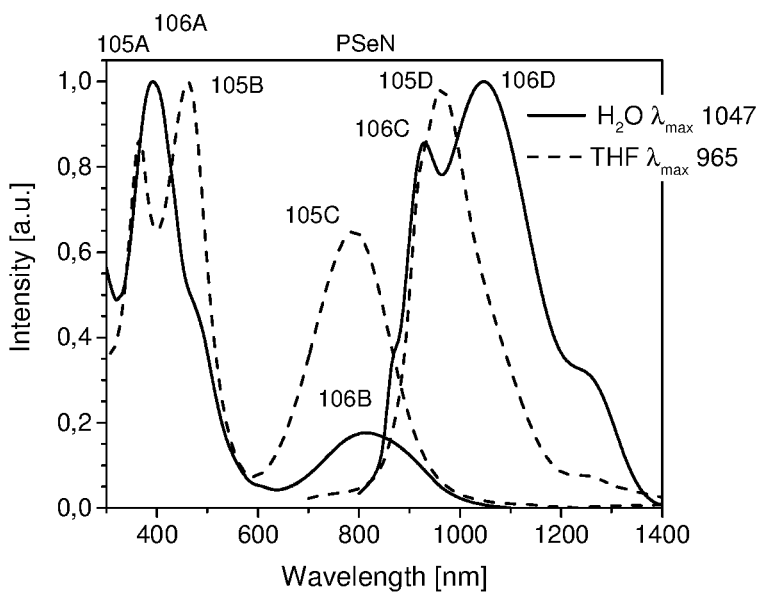

FIG. 1B shows that the absorption spectra of PSeN has three major peaks located in visible (VIS) range with a maximum at 367 nm (105A), 462 nm (105B) and 788 nm (105C) for PSN CP in THF and two peaks 392 min. (106A) and 815 nm (106B) for PSN Pdots in water. The PSN emission have maximum at 960 nm (105D) for PSN CP in THF and double maximum at 930 nm (106C) and 1.047 nm (106D) for PSN Pdots in water.

Figure 1C:
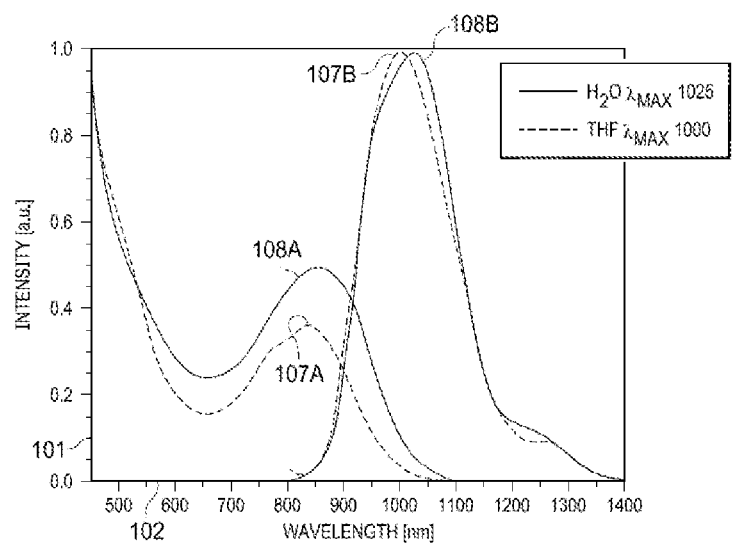

FIG. 1C shows that the most far-red shifted carbazole-based conjugated polymer, CBz-BBT, has absorption bands in the NIR range with a maximum at 835 nm (107A) for CBz-BBT CP in THF and 858 rim (108A) for CBz-BBT Riots in water. The emission spans the range between 850 nm and 1.350 nm with the peak maxima at 1,000 nm (107B) for CBz-BBT CP in THF and 1,025 nm (108B) for CBz-BBT Pdots in water. Once more, the wavelength range of the fluorescence occurs in the range for imaging in the second tissue transparent spectral window. This, together with suitability of excitation at first tissue transparent window, makes the Pdots suitable for use with in vivo deep tissue imaging applications.

Figure 1D:
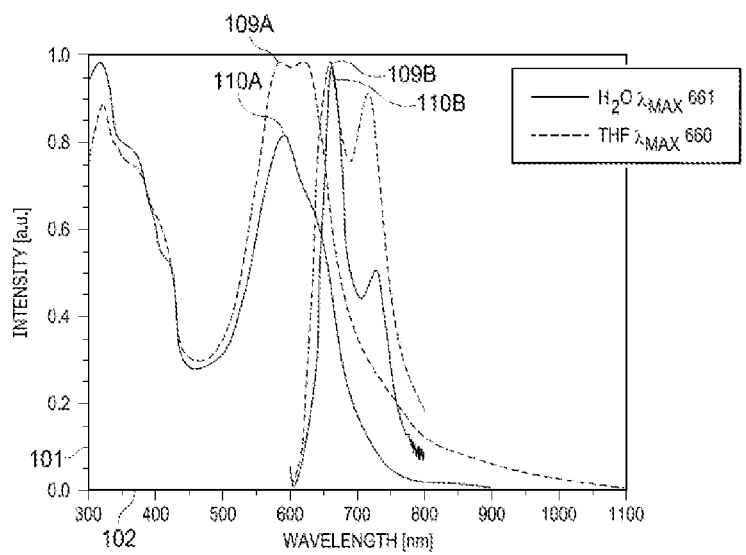

FIG. 1D shows that the most blue-shifted carbazole-based conjugated polymer, CBz-DPP, has a broad absorption band at 619 nm (109A) for CBz-DPP CP in THF and a peak at 590 nm (110A) for CBz-DPP Pdots dispersed in water. The emissions coincide with the first tissue transparent window and with emission maxima at 661 nm (110B) for CBz-DPP Pdots dispersed in water and 660 nm (109B) for CBz-DPP CP in THE.

Figure 1E:
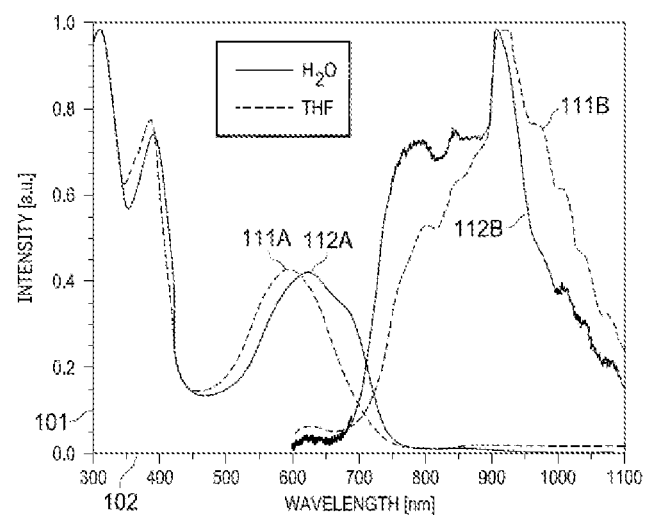
Figure 1F:
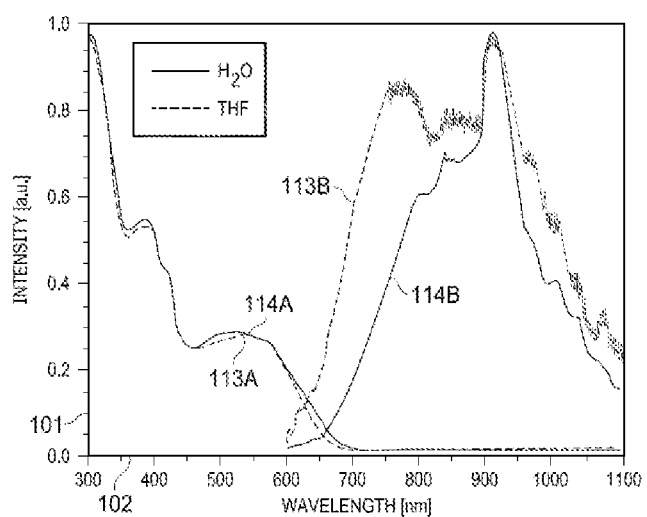

As shown in FIG. 1E, there is an absorption maximum at 593 nm (111A) for CBz-NDI CP in THE and 624 nm (112A) for CBz-NDI Riots in water. The emission for both CBz-NDI CP in THE (111B) and CBz-NDI Pdots (112B) spans the range of 700-1,100 nm. As shown in FIG. 1F, the CBz-isoindigo CP has a maximum of absorption at 545 nm (113A) in THE and 526 nm (114A) for CBz-isoindigo Pdots in water, with the emission spanning the range between 650 nm and 1,100 nm for both CBz-NDI CP in THF (113B) and CBz-NDI Pdots (114B), in the case of CBz-NDI and CBz-isoindigo, it was not possible to record accurate fluorescence spectra since the maximum of their emission falls between the edges of low detection sensitivity of the Si- and InGaAs-based photodetectors used for testing.

Scanning confocal fluorescence microscopy images of PSN Pdots deposited on a glass and recorded with Si-based avalanche photodiode (detection in the FR/NIR) or InGaAs-based avalanche photodiode (detection in the SWIR) show that the Pdots were generally spherical.

Figure 2A:
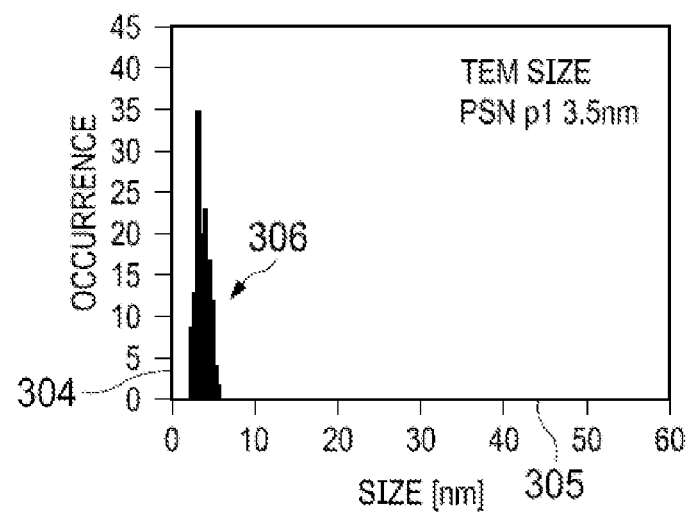
FIGS. 2A-2C are column graphs showing the size distributions of Pdots from three different preparations.
Figure 2B:
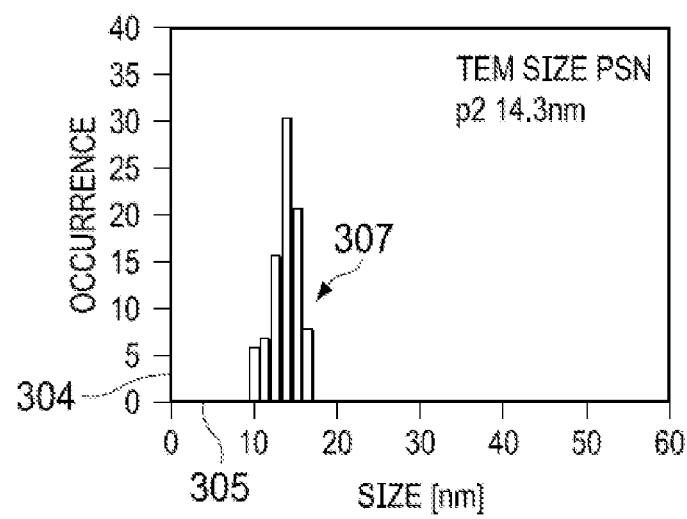
Figure 2C:
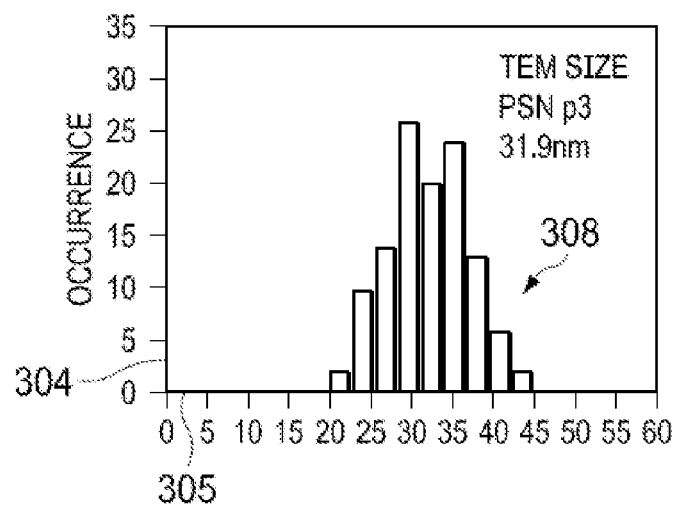

FIGS. 2A-2C show the data for the size distributions of PSN Pdots prepared from Preparations 1, 2, and 3. The data show that varying the volume ratio of conjugated polymer-THE solution to water allowed preparation of nanoparticles with controlled sizes. FIG. 2A is a frequency histogram (scale=50 rim) of the PSN Pdot size distribution of Preparation 1 from the 1:10 mixing ratio of the PSN-THF solution and water. The average size of the Riots with a 1:10 mixing ratio was 3.5 nm with a distribution range (306) of approximately from 2.0 cm to 5.0 cm. FIG. 2B is a frequency histogram (scale=100 nm) of the PSN Pdot size distribution of Preparation 2 from the 1:1 mixing ratio of the PSN-THF solution and water. The average size of the Pdots with a 1:1 mixing ratio is 14.3 nm with a distribution range (307) of approximately from 9.0 nm to 16.0 nm FIG. 2C is a frequency histogram (scale=100 nm) of the PSN Pdot size distribution of Preparation 3 from the 2:1 mixing ratio of the PSN-THF solution and water. The average size of the Pdots with a 2:1 mixing ratio is 31.9 nm with a distribution range (308) of approximately from 20.0 nm to 45.0 nm Example 2: Size Independent Optical Properties of the FRINIR and SW IR Emitting Conjugated Polymer Nanoparticles Methods Pdots Size Determination TEM images of the Pdots were produced by an FEI Tecnai G2 Spirit TWIN microscope. The samples for the TEM measurements were prepared by dropcasting colloidal solutions of the Pdots onto a holey carbon film on copper grids (EMS, Q225-CMA). The TEM grids were treated with plasma before sample preparation.

Steady-state absorption and fluorescence measurements were performed in a U-3900 Spectrometer (Hitachi HighTechnologies) to collect absorption spectra. Fluorescence spectra were recorded with Isoplane SCT320 spectrograph (Princeton Instruments) equipped with liquid nitrogen cooled IR camera PyLoN 1024/1.7. Sample was inserted in CVH100 Cuvette Holder (Thorlabs) equipped with longpass edge filter FELH0850, collimating optic and fiber adapter, allowing the cuvette holder to be directly connected to spectrograph. Samples were excited with 785 CW laser diode module LDM785 (Thorlabs). All spectra were background corrected by subtracting the scattering response from the solvent. The fluorescence quantum yield (QY) was determined using IR-E1050 dye (NirMidas Biotech) as reference standard (QY-2%). Fluorescence quantum yields were calculated from the gradients of linear relation between absorbance and integrated fluorescence intensities recorded for five different sample dilution, according to the following equation:

$$\Phi_x = \Phi_{ST}\left(\frac{Grad_x}{Grad_{ST}}\right)\left(\frac{\eta_x^2}{\eta_{ST}^2}\right)$$

where the subscripts ST and X denote standard and tested sample respectively, Φ is the fluorescence quantum yield. Grad the gradient from the plot of integrated fluorescence intensity vs. absorbance, and η the refractive index of the solvent.

Results

The increase in the size of the Pdots has little effect on their photophysical properties, which are properties determined by photoexcitation and subsequent processes without involving chemical change. Absorption spectra of PSN Pdots with three different sizes (3.5, 14.3, and 31.9 nm in diameter) show only slight broadening as the size of the Pdots increases. The fluorescence spectra remain unchanged with increasing Pdot size, which is a very desirable property for some applications. This feature gives the claimed Pdots another distinct advantage over the quantum dot-based NIR/SWIR emitters, which have size-dependent photophysical properties.

Figure 3A:
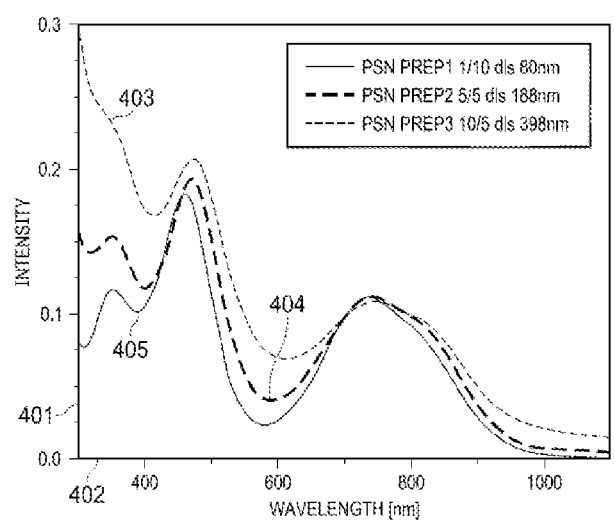
FIGS. 3A and 3B are line graphs of the UV-VIS-FR/NIR/SWIR absorption (FIG. 3A) and emission (FIG. 3B) spectra of PSN Pdots of three different diameters (3.5 nm, 14.3 nm, and 31.9 nm) in water.

FIG. 3A shows UV-VIS-NIR absorption spectra of three different sizes (3.5 nm, 14.3 nm, and 31.9 nm in diameter) of the PSN Pdots in water with intensity (401) plotted against wavelength (402). The absorption spectra of the Pdots sized at 3.5 nm (405), 14.3 nm (404) and 31.9 nm (403) show only a slight broadening as the Pdot size increases.

Figure 3B:
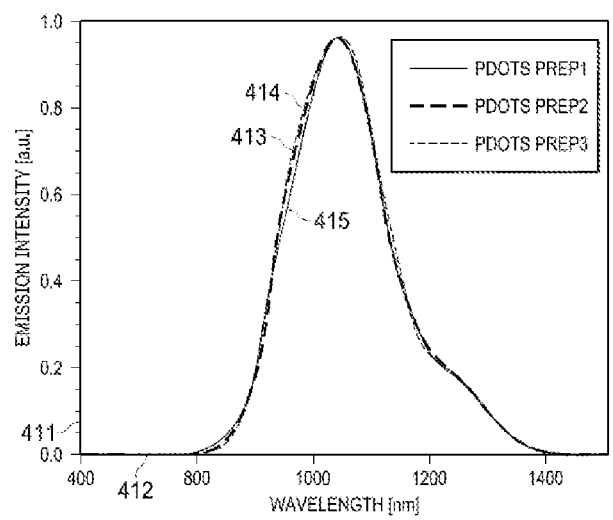

FIG. 3B shows fluorescence spectra of three different sizes (3.5 nm, 14.3 nm, and 31.9 nm in diameter) of the PSN Pdots in water with emission intensity (411) plotted against (wavelength). As shown in FIG. 3B, the fluorescence spectra for all three of the preparations, 3.5 nm (415), 14.3 nm (414) and 31.9 nm (413), remained the essentially the same, regardless of the Pdot size.

The quantum yields of Pdots described herein were compared with those of other nanoparticles, Table 1.

TABLE 1

Fluorescence quantum yields of PSN[a], PCBzBBT[b], and PSeN[c]

| Nanoparticle | Fluorescence quantum yield (%) | Fluorescence lifetime |
|---|---|---|
| PSN | 7.75 (THF)/0.31 (Pdots in $H_2O$) | 0.68 ns (THF)/0.83 ns Pdots in water) |
| PCBz-BBT | 1.76 (THF)/0.29 (Pdots in $H_2O$) | 1.15 ns (THF)/0.38 ns |
| PSeN | 1.35 (THF)/0.016 (Pdots in $H_2O$) | 0.56 ns (THF)/1.1 ns (Pdots in water) |
| IR26[d] | 0.05 | |
| Organic dye[e] | 0.03 | |
| IR-E1050 dye doped PS beads (Nirmidas Biotech) | 0.2 | 1.27 |
| Pdot[f] | 0.17 | |
| $Ag_2S$ quantum dot | up to 3 | 60 ns |
| PbS quantum dot | up to 8 | between 1 and 2 µs |
| InAs-CdSe quantum dot[g] | up to 30 | 100 ns |

[a]3.5-nm, 14.3-nm, and 31.9-nm particles were used.
[b]3.9-nm particles were used.
[c]2.7-nm particles were used.
[d]4-[2-[2-Chloro-3-[(2-phenyl-4H-1-benzopyran-4-ylidene)ethylidene]-1-cyclohexen-1-yl]ethenyl]-2-phenyl-1-benzopyrylium perchlorate
[e]Nat Mater. (2016); 15,235-42; DOI: 10.1038/nmat4476
[f]Nat. Commun. (2014); 5, 4206; DOI: 10.1038/ncomms5206
[g]Nat Biomed Eng. 2017; 1: 0056.; DOI:10.1038/s41551-017-0056

The fluorescence quantum yields of the fabricated Pdots are not dependent on their sizes. The fluorescence quantum yields of the PSN and PCBzBBT Pdots (0.31 and 0.29% in water) are higher than previously reported SWIR emitting Pdots (0.17%, Nat. Commun. (2014); 5, 4206).

Example 3: Photoluminescence Intensity as a Function of Time

Materials

PbS core-type quantum dots Xem 1000 nm and (3-Aminopropyl)-triethoxysilane were obtained from Sigma Aldrich.

Methods

Single-particle fluorescence measurements were conducted on a home-built scanning confocal microscope based on an Olympus IX 71 platform. A CW laser diode operating at 785 nm (Cobolt, 08-01 Series) was used as the excitation source in the scanning confocal microscope setup. The circularly polarized excitation light was obtained using a λ/4 wave plate (Thorlabs; WPQ10M), and the laser intensity was tuned by neutral density filters (Thorlabs, FW2AND). The excitation light was expanded by a beam expander to fill the back aperture of the objective lens before introducing the light into the microscope. The samples for all the single-particle measurements were prepared by depositing colloidal solutions of the Pdots or Qdots on silanized surface of clean coverslips. The samples were excited through a high numerical aperture (NA) oil immersion objective (UPlanSApo, 100, NA 1.40, Olympus). Raster scanning of the samples was achieved by moving the objective with a precision piezoelectric translation stage (Physik Instrumente, P-733.2CL,) controlled by a digital piezo controller (Physik Instrumente, E-710.4CL). Fluorescence from the samples was collected by the same objective, passed through a single-edge laser dichroic beamsplitter (Semrock, Di02-R830). For the measurements of single-particle fluorescence intensity time trajectories, the fluorescence signal obtained under the same excitation conditions and separated from the remaining excitation light by a long-pass emission filter (Chroma, RET 792 LP) was split into two channels on short-pass dichroic mirror (Thorlabs, DMSP950R) and simultaneously detected by a (Si) single photon avalanche photodiode (SPAD, PicoQuant, t-SPAD-50,) equipped with razor edge ultra-step emission filter (Semrock, LP02-830RE) and (InGaAs) single photon avalanche photodiode (MPD Micro Photon Devices, InGaAs/InP). Further recorded by the TCSPC module (PicoQuant, HydraHarp 400) in the time-tagged time-resolved mode.

Results

Figure 4A:
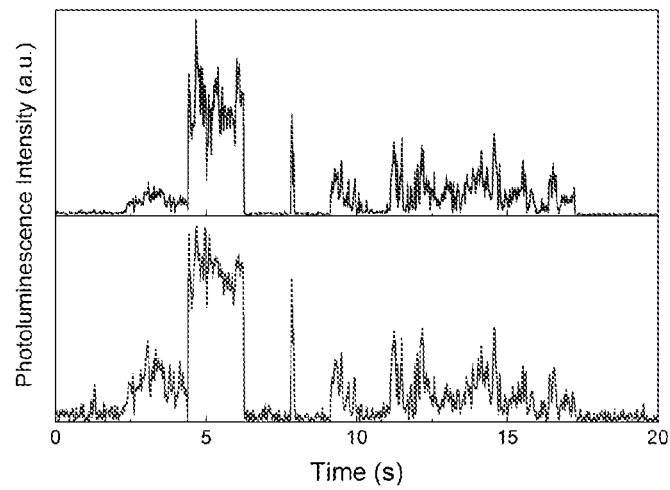
FIGS. 4A and 4B are line graphs showing the photoluminescence intensities of a quantum dot (FIG. 4A) and a Pdot (FIG. 4B) as a function of time. The excitation wavelength is 785 nm.
Figure 4B:
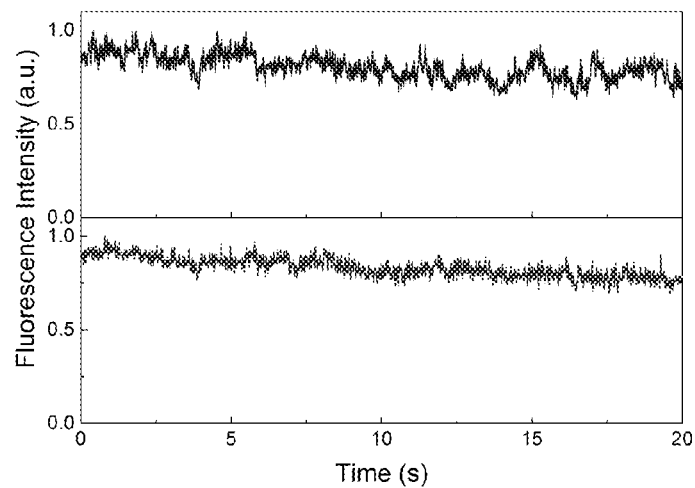

Referring to FIGS. 4A and 4B, the photoluminescence intensity time trajectories of a single PbS quantum dot (4.2 nm) was compared to that of single PSN Pdots (3.5 nm). The PbS quantum dot and PSN Pdots were deposited on separate glass coverslips and their photoluminescence time trajectories were captured by both Si-based photodetector (visible wavelength region, top) and InGaAs-based photodetector (SWIR region, bottom). The excitation wavelength is 785 nm. The trajectories of the PbS quantum dot showed large intensity fluctuations, FIG. 4A. In contrast, the trajectories of the PSN Pdots showed nearly constant fluorescence intensity over time, FIG. 4B.

Example 4: Excitation Power-Dependent Fluorescence Intensifies of Single SWIR-Emitting Pdots Materials PS beads loaded with IR-E1050 dye were obtained from NirMidas Biotech. PbS core-type quantum dots λem 1000 nm were obtained from Sigma Aldrich.

Methods

Single-particle fluorescence measurements were conducted on a home-built scanning confocal microscope based on an Olympus IX 71 platform. A CW laser diode operating at 785 nm (Cobolt, 08-01 Series) was used as the excitation source in the scanning confocal microscope setup. The circularly polarized excitation light was obtained using a λ/4 wave plate (Thorlabs; WPQ10M), and the laser intensity was tuned by neutral density filters (Thorlabs, FW2AND). The excitation light was expanded by a beam expander to fill the back aperture of the objective lens before introducing the light into the microscope. The samples for all the single-particle measurements were prepared by depositing colloidal solutions of the Pdots or Qdots on silanized surface of clean coverslips. The samples were excited through a high numerical aperture (NA) oil immersion objective (UPlanSApo, 100, NA 1.40, Olympus). Raster scanning of the samples was achieved by moving the objective with a precision piezoelectric translation stage (Physik Instrumente, P-733.2CL,) controlled by a digital piezo controller (Physik Instrumente, E-710.4CL). Fluorescence from the samples was collected by the same objective, passed through a single-edge laser dichroic beamsplitter (Semrock, Di02-R830). For the measurements of single-particle fluorescence intensity time trajectories, the fluorescence signal obtained under the same excitation conditions and separated from the remaining excitation light by a long-pass emission filter (Chroma, RET 792 LP) was split into two channels on short-pass dichroic mirror (Thorlabs, DMSP950R) and simultaneously detected by a (Si) single photon avalanche photodiode (SPAD, PicoQuant, t-SPAD-50,) equipped with razor edge ultra-step emission filter (Semrock, LP02-830RE) and (InGaAs) single photon avalanche photodiode (MPD Micro Photon Devices, InGaAs/InP). Further recorded by the TCSPC module (PicoQuant, HydraHarp 400) in the time-tagged time-resolved mode. The brightness of the fluorescence of single particles was estimated by measuring fluorescence images of the individual particles under identical excitation and detection conditions and calculating the integrated intensity of each fluorescence spot.

Results

Referring to FIG. 5, the commercially available PbS quantum dot showed the lowest count rates at all the excitation power. The commercially available polystyrene (PS) nanoparticles containing organic dye IR-E1050 (200 nm in diameter, Nirmidas Biotech) showed highest fluorescence count rates at lower excitation power. This dye-incorporated PS beads is the only commercially available organic SWIR-emitting nanoparticles. The PSN Pdots (30 nm in diameter) showed the highest fluorescence count rates at higher excitation power. Note that the volume of the 30-nm PSN Pdots is approximately 300 times smaller than that of the 200-nm commercially available dye-incorporated PS beads, demonstrating that the PSN Pdots showed very high fluorescence signal per unit volume. The PSN Pdots (3 nm in diameter) show higher fluorescence count rates compared with the commercially available PbS quantum dots. Larger saturation excitation power is desired for single-particle fluorescence imaging as this allows for higher fluorescence count rates at a high excitation power.

Referring to FIG. 6, saturation intensities (Is) were determined using the fittings shown in FIG. 5. The commercially available dye-incorporated PS beads (200 nm in diameter) show lowest saturation intensity (19 kWcm$^{-2}$). The PSN Pdots show higher saturation intensities (227-514 kWcm$^{-2}$) than the commercially available PbS quantum dots (104 kWcm$^{-2}$). The smaller PSN Pdots show higher saturation intensity than the larger PSN Pdots.

Referring to FIG. 7, fluorescence count rates were obtained for the nanoparticles referenced in FIGS. 5 and 6, at different excitation powers. The commercially available dye-incorporated PS beads (200 nm in diameter) showed highest fluorescence intensity up to 59.4 kWcm$^{-2}$ excitation power. The PSN Pdots (30 nm in diameter) showed highest fluorescence intensity above 509 kWcm$^{-2}$. The maximum fluorescence intensity of the PSN Pdots (30 nm in diameter) was almost 3-times higher than that obtained from the commercially available dye-incorporated PS beads (200 nm in diameter) (40.4 kcnts per sec and 15.5 kcnts per sec, respectively).

Example 5: Single-Molecule Fluorescence Imaging at Different Depths

Materials

Sylgrad 184 Silicone elastomer was obtained from Dow Corning. Nigrosin, soluble in spirit was obtained from Alfa Aesar. Instant coffee was NESCAFE™ coffee. Titanium (IV) oxide was obtained from Aldrich.

Methods

Single-molecule fluorescence images of PSN Pdots (30 nm in diameter) were captured by Si-based and InGaAs-based photodetectors. A 785-nm laser was used as an excitation light at 228 kWcm$^{-2}$ power. Fluorescence images were recorded at a stage-scan speed of 1-ms per pixel. The PSN Pdots were deposited on tissue phantoms with different thicknesses: 0.14 mm, 0.27 mm, 0.78 mm, and 1.27 mm Fluorescence images were detected through the tissue phantoms. A schematic illustration of the experimental set up is shown in FIG. 8. The tissue phantoms contain polydimethylsiloxane containing 10 mg/mL instant coffee (absorbing agent, target absorption at 650 nm: 0.2 mm$^{-1}$) and 2 mg/mL TiO$_2$ particles (scattering agent, target reduced scattering at 650 nm: 3 mm$^{-1}$)) and mimic the epidermis. (Saager, et al., Proc. SPIE 2010, 7567, 756706.

Results

Fluorescence signal from a single PSN Pdots (30 nm in diameter) can be detected through the 1.27-mm thick tissue phantom. Further, 14-nm PSN Pdots were detected through 0.8-mm thick tissue phantom, demonstrating the applicability of the PSN Pdots in single-particle deep tissue fluorescence imaging (e.g., Bruns, et al., Nat. Biomed. Eng., 2017; doi: 10.1038/s41551-017-0056; Godin, et al. Nat. Nanotechnol. 2017, 12, 238-243).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A conjugated polymer having the structure:

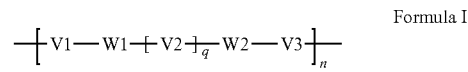

Formula I wherein:
n is an integer between 1 and 10,000, inclusive;
q is an integer between 1 and 5, inclusive,
V1, V2, and V3 are independently absent, carbon-carbon double bond, carbon-carbon triple bond, unsubstituted heteroaryl, substituted heteroaryl, unsubstituted aryl, or substituted aryl; wherein
(A) W1 is

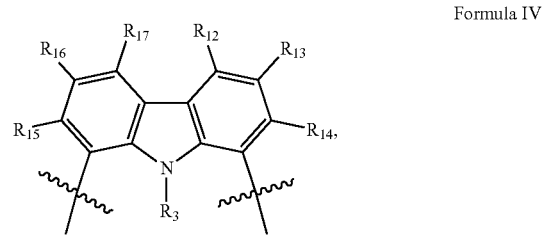

Formula IV wherein R$_3$ is hydrogen, unsubstituted alkyl, or substituted alkyl,
wherein R$_{12}$, R$_{13}$, R$_{14}$, R$_{15}$, R$_{16}$ and R$_{17}$ are independently substituted alkyl, unsubstituted alkyl, hydrogen, unsubstituted aryl, substituted aryl, unsubstituted heteroaryl, substituted heteroaryl, hydroxyl, or halogen, and W2 is selected from

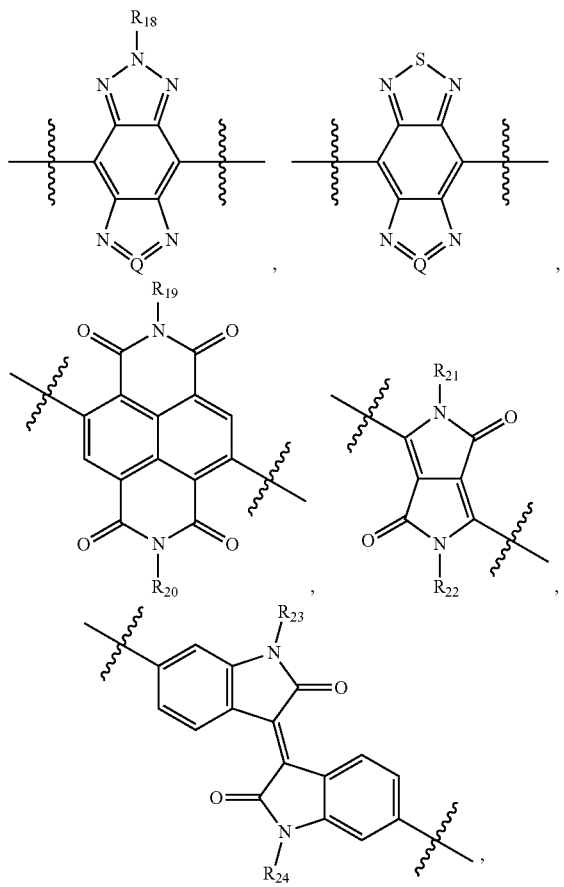

or a combination thereof,
Q is sulfur or selenium;
wherein $R_{18}$, $R_{19}$, $R_{20}$, $R_{21}$, $R_{22}$, $R_{23}$, and $R_{24}$ are independently unsubstituted alkyl, substituted alkyl, or hydrogen;
at least one of V1, V2, and V3 is a carbon-carbon double bond; carbon-carbon triple bond, substituted heteroaryl, unsubstituted aryl, or substituted aryl;
when $R_{21}$ and $R_{22}$ are $C_8H_{17}$, either (i) $R_3$ is a hexadecyl or (ii) $R_{13}$ and $R_{16}$ are substituted alkyl or unsubstituted alkyl;
or
(B) W1 is Formula III

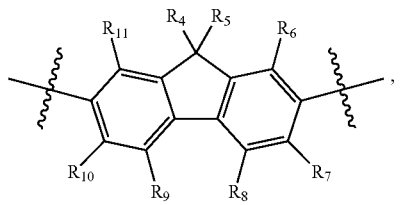

wherein $R_4$, and $R_5$ are independently hydrogen, unsubstituted alkyl, or substituted alkyl,
wherein $R_6$, $R_7$, $R_8$, $R_9$, $R_{10}$, and $R_{11}$ are independently hydrogen, unsubstituted alkyl, substituted alkyl, unsubstituted aryl, substituted aryl, unsubstituted heteroaryl, substituted heteroaryl, hydroxyl, or halogen, and W2 is selected from

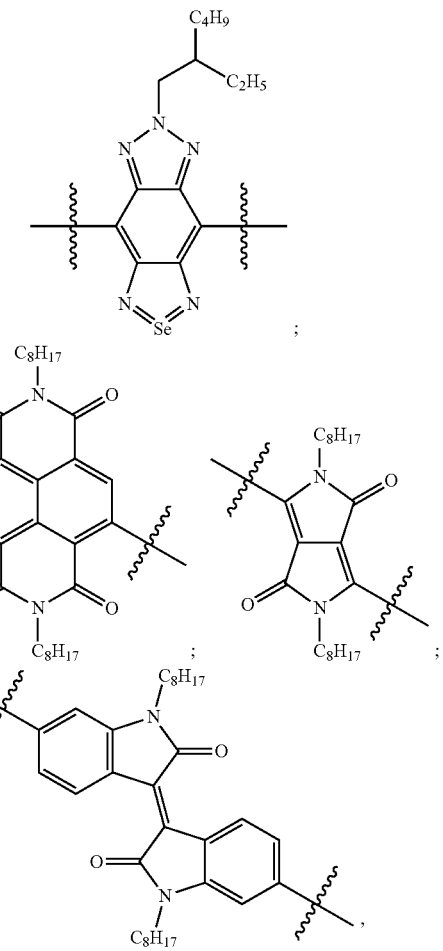

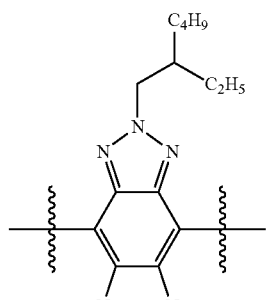

or

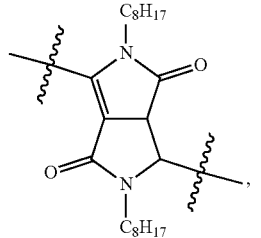

and optionally,
wherein, when $R_4$ and $R_5$ are $C_8H_{17}$, and $R_6$, $R_7$, $R_8$, $R_9$, $R_{10}$, and $R_{11}$ are hydrogen, W2 is not and optionally,
wherein, the substituents of the substituted chemical groups are selected from the group consisting of alkyl, alkenyl, alkynyl, aryl, heteroaryl, hydroxyl, halogen, alkoxy, aroxy, alkylthio, arylthio, cyano, isocyano, carbonyl, carboxyl, amino, amido, sulfonyl, sulfonic acid, phosphoryl, phosphonyl, polyaryl, unsubstituted $C_3$-$C_{20}$ cycloalkyl, and unsubstituted heterocyclyl.

2. The conjugated polymer of claim 1, having an emission maximum of light in the far-red, near-infrared, or short-wavelength infrared region of the electromagnetic spectrum, or a combination thereof.

3. The conjugated polymer of claim 1, wherein X is $CR^4R^5$ or $NR^3$, $R_3$, $R_4$, and $R_5$ are independently unsubstituted alkyl or substituted alkyl.

4. The conjugated polymer of claim 1, wherein W1 is:

(A)

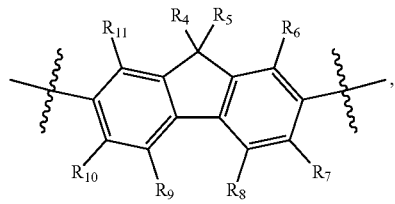

Formula III wherein $R_6$, $R_7$, $R_8$, $R_9$, $R_{10}$, and $R_{11}$ are independently hydrogen, unsubstituted alkyl, substituted alkyl, unsubstituted aryl, substituted aryl, unsubstituted heteroaryl, substituted heteroaryl, hydroxyl, or halogen;

(B)

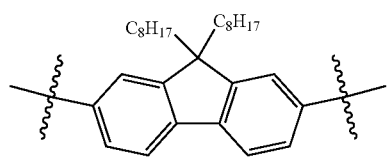 or (C)

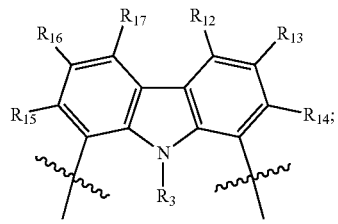

wherein $R_{12}$, $R_{13}$, $R_{14}$, $R_{15}$, $R_{17}$, and $R_{17}$ are independently substituted alkyl, unsubstituted alkyl, hydrogen, unsubstituted aryl, substituted aryl, unsubstituted heteroaryl, substituted heteroaryl, hydroxyl, or halogen, and $R_{12}$, $R_{14}$, $R_{15}$, and $R_{17}$ are hydrogen;

and optionally, wherein $R_{13}$ and $R_{16}$ are $C_1$-$C_{10}$ substituted alkyl, and $R_{12}$, $R_{14}$, $R_{15}$, and $R_{17}$ are hydrogen; and V1 or at least one V2 is a triple bond.

5. The conjugated polymer of claim 1, wherein:
(A) q is 2; V1, V2, V3 are independently a carbon-carbon triple bond, unsubstituted heteroaryl, or substituted heteroaryl,
or
(B) q is 1; V1 and V2 are carbon-carbon triple bonds; and V3 is absent.

6. The conjugated polymer of claim 1, wherein W1 is

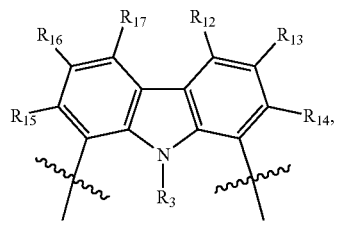

Formula IV wherein $R_{12}$, $R_{13}$, $R_{14}$, $R_{15}$, $R_{17}$, and $R_{17}$ are independently substituted alkyl, unsubstituted alkyl, hydrogen, unsubstituted aryl, substituted aryl, unsubstituted heteroaryl, substituted heteroaryl, hydroxyl, or halogen, wherein W2 is selected from

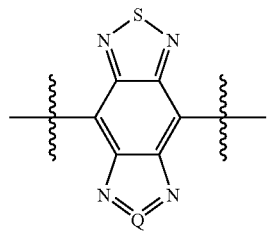

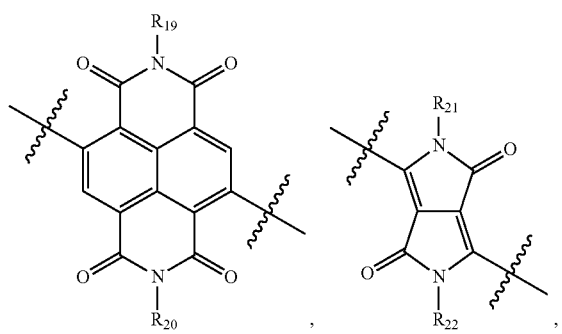

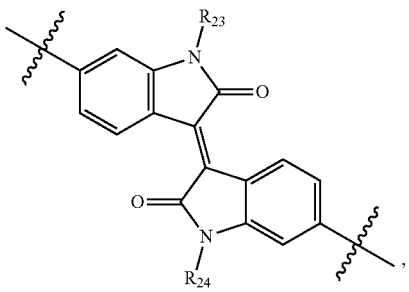

or a combination thereof,

Q is sulfur or selenium; and $R_{19}$, $R_{20}$, $R_{21}$, $R_{22}$, $R_{23}$, and $R_{24}$ are independently $C_1$-$C_{10}$ unsubstituted alkyl.

7. A conjugated polymer, having the structure:

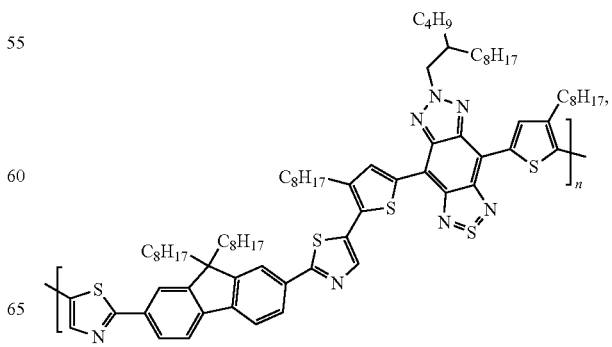

-continued

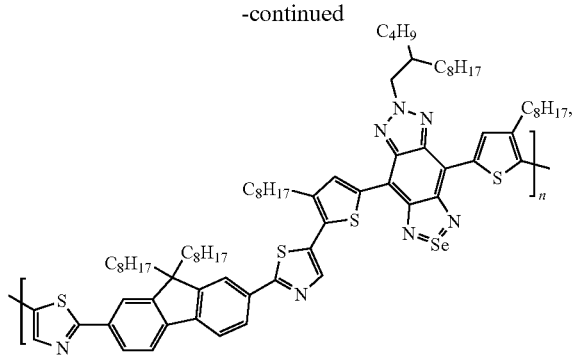

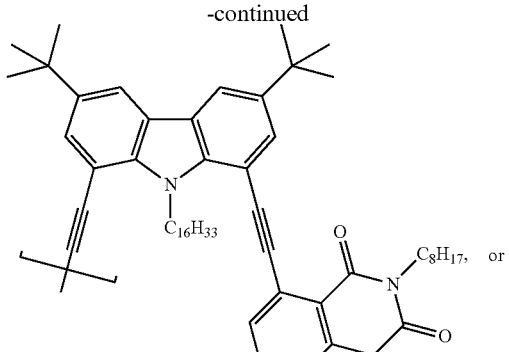

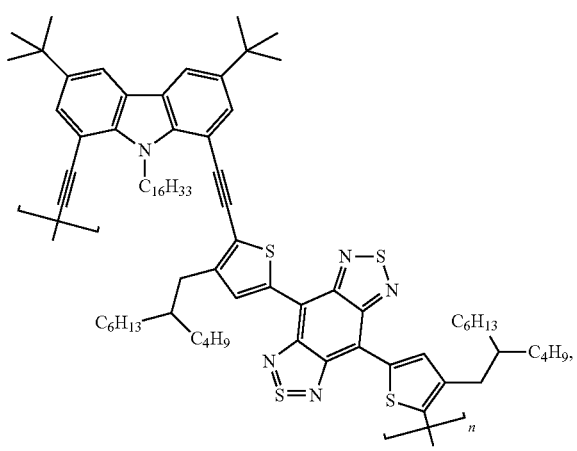

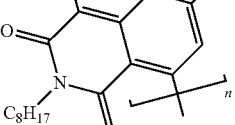

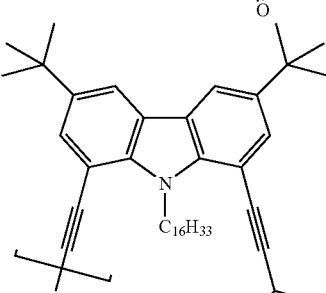

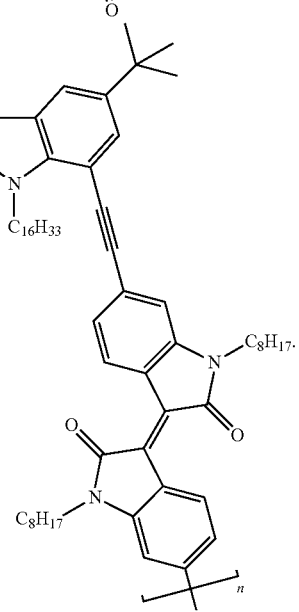

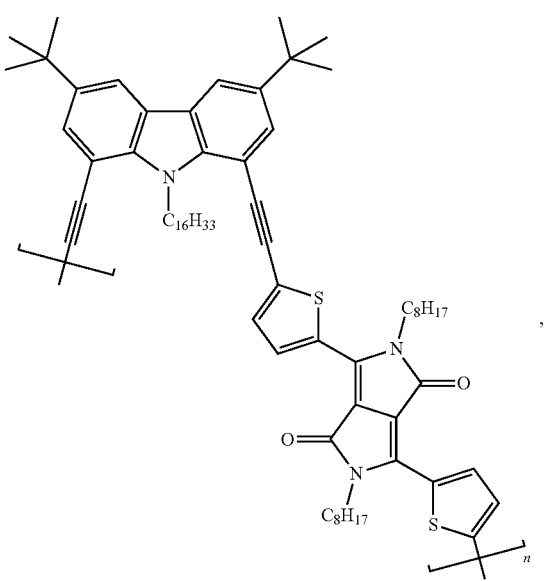

8. The conjugated polymer of claim 2, wherein the emission maximum of light is between 650 nm and 1,350 nm, inclusive.

9. A conjugated polymer nanoparticle comprising the conjugated polymer of claim 1.

10. The conjugated polymer nanoparticle of claim 9, (i) wherein the conjugated polymer nanoparticles have an emission maximum of light in the far-red, near-infrared, or short-wavelength infrared region of the electromagnetic spectrum, or a combination thereof, and optionally, wherein conjugated polymer nanoparticles have a light emission spectrum that is independent of nanoparticle size; or (ii) having a diameter between 1.0 nm and 100 nm.

11. The conjugated polymer nanoparticle of claim 10, wherein the emission maximum of light has a wavelength between 650 nm and 1,350 nm, inclusive, between 600 nm and 1,350 nm, inclusive, between 600 nm and 1,100 nm, inclusive, or between 650 nm and 1,100 nm, inclusive.

12. A method of making a conjugated polymer nanoparticle comprising:
(a) dissolving the conjugated polymer of claim 1 in an organic solvent;
(b) optionally creating a saturated conjugated polymer solution;
(c) filtering the solution from step (b); and
(d) mixing the solution from step (c) with water or aqueous solvent and at a temperature between 0° C. and 10° C., to form conjugated polymer nanoparticles.

13. The method of claim 12, wherein: (i) the conjugated polymer nanoparticles have an emission maximum of light in the far-red, near-infrared, or short-wavelength infrared region of the electromagnetic spectrum, or a combination thereof; (ii) step (c) is performed using a polycarbonate filter; (iii) the sonication at step (a) is carried out at a frequency between 30 kHz and 45 kHz, inclusive; (iv) the conjugated polymer nanoparticles have a diameter between 1.0 nm and 100 nm.

14. The method of claim 13, wherein: (i) the emission maximum of light has a wavelength between 650 nm and 1,350 nm; or (ii) the polycarbonate filter has a pore size of between 0.05 μm and 0.45 μm.

15. The method of claim 12, (A) wherein the organic solvent is tetrahydrofuran and/or (B) comprising changing the volumetric ratio of the solution from step (c) and the water in step (d) to adjust the diameter of the conjugated polymer nanoparticle.

16. A method of imaging a biological sample, the method comprising:
(a) administering to the biological sample an effective amount of the conjugated polymer nanoparticle of claim 9 to produce an emission spectrum; and
(b) exposing the biological sample from step (a) to light.

17. A conjugated polymer having the structure:

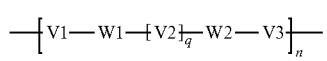

Formula I wherein:
n is an integer between 1 and 10,000, inclusive;
q is an integer between 1 and 5, inclusive;
W1 has the structure:

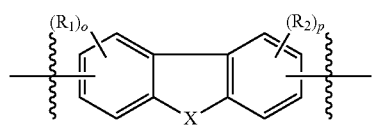

Formula II o and p are independently integers between 1 and 3, inclusive;

$R_1$ and $R_2$ are independently hydrogen, unsubstituted alkyl, substituted alkyl, unsubstituted aryl, substituted aryl, unsubstituted heteroaryl, substituted heteroaryl, hydroxyl, or halogen, or $R_1$ and $R_2$ are substituted alkyl;

X is O or S;

W2 is one or more polycyclic ring systems, having an unsubstituted heterocycle, substituted heterocycle, unsubstituted heteroaryl, or substituted heteroaryl, unsubstituted aryl, or substituted aryl, V1, V2, and V3 are independently absent, carbon-carbon double bond, carbon-carbon triple bond, unsubstituted heteroaryl, substituted heteroaryl, unsubstituted aryl, or substituted aryl; and wherein, the substituents of the substituted chemical groups are selected from the group consisting of alkyl, alkenyl, alkynyl, aryl, heteroaryl, hydroxyl, halogen, alkoxy, aroxy, alkylthio, arylthio, cyano, isocyano, carbonyl, carboxyl, amino, amido, sulfonyl, sulfonic acid, phosphoryl, phosphonyl, polyaryl, unsubstituted $C_3$-$C_{20}$ cycloalkyl, and unsubstituted heterocyclyl.

18. The polymer of claim 1, wherein $R_3$, $R_4$, $R_5$, $R_{13}$, $R_{16}$, $R_{18}$, $R_{19}$, $R_{20}$, $R_{21}$, $R_{22}$, $R_{23}$, and $R_{24}$ are unsubstituted alkyl; $R_6$, $R_7$, $R_8$, $R_9$, $R_{10}$, and $R_{11}$ are hydrogen; and or the substituents of the substituted chemical groups are selected from the group consisting of alkyl, alkenyl, alkynyl, aryl, heteroaryl, hydroxyl, halogen, alkoxy, aroxy, alkylthio, arylthio, cyano, isocyano, carbonyl, carboxyl, amino, amido, sulfonyl, sulfonic acid, phosphoryl, phosphonyl, polyaryl, unsubstituted $C_3$-$C_{20}$ cycloalkyl, and unsubstituted heterocyclyl.

19. The conjugated polymer of claim 5, wherein:
V1 is a carbon-carbon triple bond or unsubstituted heteroaryl;
V2 is:
(i) a carbon-carbon triple bond, or
a combination of
(ii) unsubstituted heteroaryl and substituted heteroaryl,
(iii) carbon-carbon triple bond and substituted heteroaryl, or
(iv) carbon-carbon triple bond and unsubstituted heteroaryl; and
V3 is absent, an unsubstituted heteroaryl or substituted heteroaryl.

* * * * *